(12) United States Patent
Yamada

(10) Patent No.: US 8,484,572 B2
(45) Date of Patent: Jul. 9, 2013

(54) CELL IMAGE DISPLAY APPARATUS, CELL IMAGE DISPLAY METHOD, AND COMPUTER PROGRAM PRODUCT

(75) Inventor: Kazuhiro Yamada, Kobe (JP)

(73) Assignee: Sysmex Corporation, Hyogo (JP)

( * ) Notice: Subject to any disclaimer, the term of this patent is extended or adjusted under 35 U.S.C. 154(b) by 214 days.

(21) Appl. No.: 12/646,785

(22) Filed: Dec. 23, 2009

(65) Prior Publication Data
US 2010/0169811 A1 Jul. 1, 2010

(30) Foreign Application Priority Data

Dec. 25, 2008 (JP) .................................. 2008-330625

(51) Int. Cl.
*G06F 3/048* (2006.01)
(52) U.S. Cl.
USPC .......................................... 715/764; 382/133
(58) Field of Classification Search
USPC .............................. 715/764; 382/133; 128/922
See application file for complete search history.

(56) References Cited

U.S. PATENT DOCUMENTS

| | | | |
|---|---|---|---|
| 4,393,466 A | | 7/1983 | Deindoerfer et al. |
| 4,523,278 A | * | 6/1985 | Reinhardt et al. ............ 382/133 |
| 5,822,447 A | | 10/1998 | Kasdan |
| 6,350,583 B1 | * | 2/2002 | Cohen et al. .................... 435/7.1 |
| 6,518,021 B1 | * | 2/2003 | Thastrup et al. ............. 435/6.19 |
| 7,684,606 B2 | * | 3/2010 | Aoki .............................. 382/133 |
| 2004/0071328 A1 | * | 4/2004 | Vaisberg et al. .............. 382/129 |
| 2006/0109343 A1 | * | 5/2006 | Watanabe et al. ............... 348/79 |
| 2006/0127881 A1 | * | 6/2006 | Wong et al. ........................ 435/4 |
| 2006/0204071 A1 | * | 9/2006 | Ortyn et al. .................... 382/133 |
| 2006/0257884 A1 | * | 11/2006 | Brawley et al. .................... 435/6 |
| 2007/0077550 A1 | * | 4/2007 | Tohma et al. ...................... 435/4 |
| 2007/0159687 A1 | * | 7/2007 | Tohma et al. ................. 359/368 |
| 2008/0201082 A1 | | 8/2008 | Tohma et al. |
| 2008/0240539 A1 | * | 10/2008 | George et al. ................. 382/133 |
| 2009/0232381 A1 | * | 9/2009 | Matsunaga et al. ........... 382/133 |
| 2009/0324050 A1 | | 12/2009 | Takagi et al. |

FOREIGN PATENT DOCUMENTS

| | | |
|---|---|---|
| EP | 0725268 A2 | 8/1996 |
| JP | 07-020124 A | 1/1995 |
| JP | 07020124 * | 1/1995 |
| JP | 2000-353246 | 12/2000 |

* cited by examiner

*Primary Examiner* — Phenuel Salomon
(74) *Attorney, Agent, or Firm* — Sughrue Mion, PLLC

(57) ABSTRACT

A cell image display apparatus comprising: a parameter value obtainer for obtaining characteristic parameter values based on a plurality of cell images obtained by imaging a sample including the plurality of cells, wherein each of the characteristic parameter values respectively indicates characteristic of each of the cells; a type determiner for determining types of the cells based on the characteristic parameter values obtained by the parameter value obtainer; a display; and a display controller for controlling the display so as to display the cell images in a sequence based on the types of the cells obtained by the type determiner and the characteristic parameter values obtained by the parameter value obtainer. A method and a computer program product are also disclosed.

11 Claims, 23 Drawing Sheets

FIG.4

| WHITE BLOOD CELL ID | BLOOD CELL TYPE | RECONFIRMATION OBJECT | NUCLEUS AREA | CYTOPLASM AREA | ... |
|---|---|---|---|---|---|
| W001 | SEG | 0 | 120 | 85 | ... |
| W002 | BASO | 0 | 105 | 110 | ... |
| W003 | LYMPH | 0 | 155 | 30 | ... |
| W004 | — | 1 | 130 | 95 | ... |
| ... | ... | ... | ... | ... | ... |

F21　F22　F23　DB2 F24　F25

SPECIMEN ID=0003

CELL IMAGE DISPLAY APPARATUS, CELL IMAGE DISPLAY METHOD, AND COMPUTER PROGRAM PRODUCT

FIELD OF THE INVENTION

The present invention relates to a cell image display apparatus which displays a cell image obtained by imaging a cell, a cell image display method, and a computer program product.

BACKGROUND

From the past, there has been known a specimen imaging apparatus that magnifies and images the stained blood smears with a microscope and analyzes the obtained images so as to classify and count the blood cells.

In Japanese Patent Publication No. H7-20124, a blood cell analyzing apparatus is disclosed which carries out automatic classification of the blood cells. In the blood cell analyzing apparatus, a blood smear is scanned by a microscope and the blood cells are detected. After the blood cells are detected, the blood cell analyzing apparatus carries out an automatic focusing. Thereafter, the blood cell images are converted into analog signals via a television camera. Various characteristic quantities required for classifying the blood cells are obtained by a characteristic parameter extracting unit on the basis of the digital image signals of the blood cells output from an analog-digital conversion circuit. In addition, an classifying unit classifies the blood cells on the basis of these characteristic quantities.

In addition, when the detected blood cell is unclear or abnormal, the blood cell analyzing apparatus stores the digital image signal in an image memory together with the specimen number or the type of the blood cell for specifying the image signal. When a user tries to carry out the review of the specimen after a plurality of the specimens are tested, the content in the image memory is read by a keyboard input, and a specific blood cell or an abnormal blood cell is displayed on the image display apparatus. Then, the displayed specific abnormal blood cell is reclassified on the basis of human judgment.

As such a specimen imaging apparatus as described above, there is an apparatus which can display a plurality of blood cell images on one screen. In this way, when a plurality of images are aligned and displayed on one screen, the user can carry out the reclassification of the plurality of the blood cells at one time.

However, in the specimen imaging apparatus according to the related art, the blood cell images are aligned in imaging sequence on the screen, but it is not the sequence in which the reclassification can be easily carried out. As a result, the reclassification is difficult to carry out, and there is a problem in that errors occur in the reclassification.

SUMMARY OF THE INVENTION

The scope of the present invention is defined solely by the appended claims, and is not affected to any degree by the statements within this summary.

A first aspect of the present invention is a cell image display apparatus comprising: a parameter value obtainer for obtaining characteristic parameter values based on a plurality of cell images obtained by imaging a sample including the plurality of cells, wherein each of the characteristic parameter values respectively indicates characteristic of each of the cells; a type determiner for determining types of the cells based on the characteristic parameter values obtained by the parameter value obtainer; a display; and a display controller for controlling the display so as to display the cell images in a sequence based on the types of the cells obtained by the type determiner and the characteristic parameter values obtained by the parameter value obtainer.

A second aspect of the present invention is a cell image display apparatus comprising: a display; and a controller being configured to perform operations, comprising (a) obtaining characteristic parameter values based on a plurality of cell images obtained by imaging a sample including the plurality of cells, wherein each of the characteristic parameter values respectively indicates characteristic of each of the cells; (b) determining cell types of the cells based on the characteristic parameter values obtained in the operation (a), and (c) controlling the display so as to display the cell images in a sequence based on the types of the cells obtained in the operation (b) and the characteristic parameter values obtained in the operation (a).

A third aspect of the present invention is a method of displaying a cell image comprising steps of: (a) obtaining characteristic parameter values based on a plurality of cell images obtained by imaging a sample including the plurality of cells, wherein each of the characteristic parameter values respectively indicates characteristic of each of the cells; (b) determining types of the cells based on the characteristic parameter value obtained in the step (a); and (c) a display controller for controlling the display so as to display the cell images in a sequence based on the types of the cells obtained in the step (b) and the characteristic parameter values obtained in the step (a).

A fourth aspect of the present invention is a computer program product comprising: a computer readable medium, and instructions, on the computer readable medium, adapted to enable a general purpose computer to perform operations comprising: (a) obtaining characteristic parameter values based on a plurality of cell images obtained by imaging a sample including the plurality of cells, wherein each of the characteristic parameter values respectively indicates characteristic of each of the cells; (b) determining types of the cells based on the characteristic parameter value obtained in the step (a); and (c) controlling the display so as to display the cell images in a sequence based on the types of the cells obtained in the step (b) and the characteristic parameter values obtained in the step (a).

BRIEF DESCRIPTION OF THE DRAWINGS

FIG. 4 is a schematic view showing the configuration of a blood cell database according to an embodiment;

FIG. 19 is a diagram showing an example of a screen on which blood cell images are aligned in imaging sequence;

FIG. 20A is diagram showing another example of a blood cell image review screen; and FIG. 20B is a diagram showing another example of a screen on which blood cell images are aligned in imaging sequence.

DETAILED DESCRIPTION OF THE PREFERRED EMBODIMENTS

Hereinafter, exemplary embodiments of the invention will be described with reference to the drawings.

In this embodiment, there is provided a specimen imaging apparatus that magnifies and images the stained blood smears by a microscope, acquires the characteristic parameters from the obtained blood cell images, and aligns and displays the plurality of blood cell images in the sequence based on the characteristic parameters.

[Configuration of Specimen Imaging Apparatus]

Figure 1:
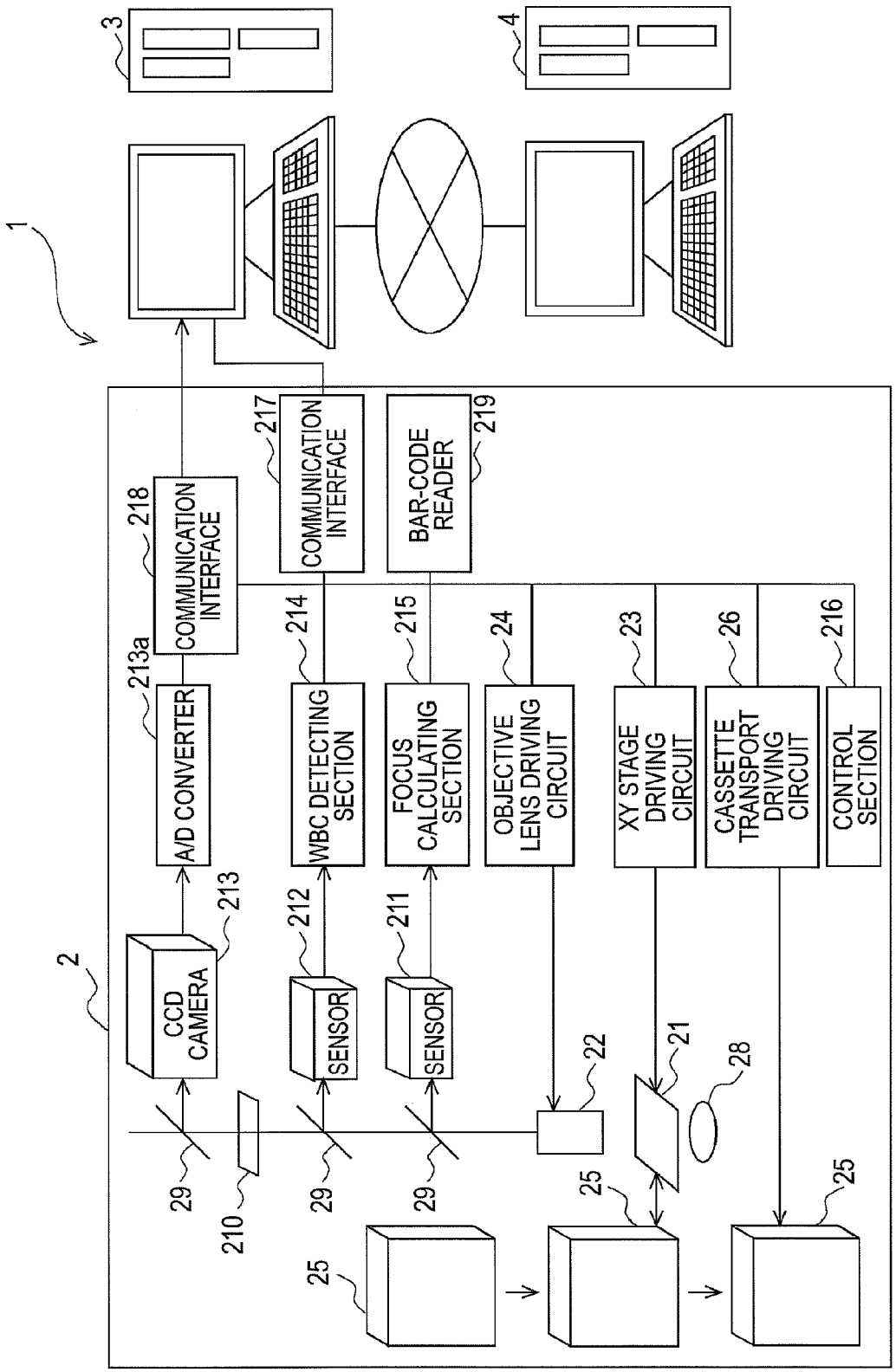
FIG. 1 is a block diagram showing the configuration of a specimen imaging apparatus according to an embodiment.

FIG. 1 is a block diagram showing the configuration of the specimen imaging apparatus according to this embodiment. FIG. 1 schematically shows the configuration of the apparatus. The arrangement of sensors, a slide cassette and the like may be slightly different from the actual arrangement to enable easier understanding. For example, in FIG. 1, a sensor for WBC detection and a sensor for auto-focusing are respectively arranged on the upper and lower sides. However, in fact, as shown in FIG. 2 to be described later, both of the sensors are arranged in substantially the same plane.

The specimen imaging apparatus 1 is provided with a microscope unit 2 which magnifies and images the blood smear to be in focus by auto-focusing, an image processing unit 3 which processes the images obtained by imaging and classifies the white blood cells in the blood from the images so as to count the number for each type of classified white blood cells, and a blood cell image display unit 4 which is connected to the image processing unit 3 and displays the images obtained by imaging and the analysis results. Further, the image processing unit 3 may not be separately configured from the blood cell image display unit 4, but both of them may be integrally configured. In addition, a smear preparing apparatus (for example, a smear preparing apparatus SP-1000i made by Sysmex Corporation) which is not shown in the drawing is disposed near the blood cell imaging apparatus 1. A blood smear prepared by the smear preparing apparatus is automatically supplied to the microscope unit 2.

<Configuration of Microscope Unit 2>

Figure 2:
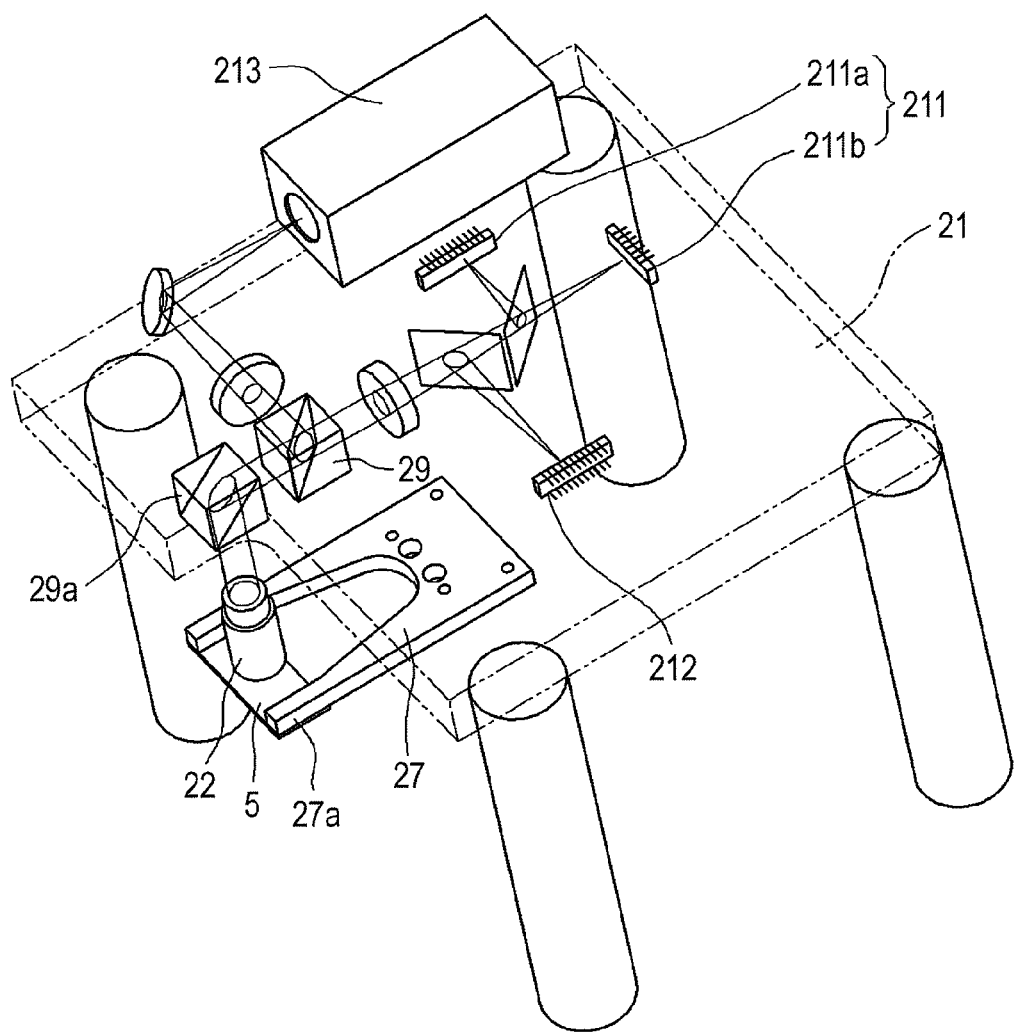
FIG. 2 is a perspective view showing a part of a microscope unit according to an embodiment.

FIG. 2 is a perspective view showing a portion of the microscope unit 2. The microscope unit 2 includes an objective lens 22 which is a portion of a lens system of a microscope magnifying an image of blood thinly spread and applied over a slide glass 5 mounted on an XY stage 21. The XY stage 21 holding a smear (the slide glass 5 with an upper surface on which the blood is smeared) can be moved back and forth and from side to side (X and Y directions) by a driving section (not shown), the driving of which is controlled by an XY stage driving circuit 23 (see FIG. 1 for reference). The objective lens 22 can be moved up and down (Z direction) by a driving section (not shown), the driving of which is controlled by an objective lens driving circuit 24.

A plurality of the slide glasses 5 are stacked and accommodated in a slide cassette 25 (see FIG. 1 for reference). The slide cassette 25 is transported by a transporting section (not shown) which is controlled by a cassette transport driving circuit 26 so as to be driven. The XY stage 21 is provided with a chuck section 27 (see FIG. 2 for reference) capable of holding two parts in the vicinities of both ends in the longitudinal direction of the slide glass 5, and the chuck section can be freely advanced and retracted with respect to the slide glass 5 accommodated in the slide cassette 25 which is stopped at a predetermined position. The chuck section 27 is advanced toward the slide cassette 25 to hold the slide glass 5 by an opening-closing operation of claw sections 27a which can be freely opened and closed and each of which is formed at the tip of the chuck section 27. Then, the chuck section 27 is retracted to draw the slide glass 5 from the slide cassette 25 so that the slide glass can be disposed at a predetermined position on the XY stage 21.

Returning to FIG. 1, a lamp 28 as a light source is disposed below the slide glass 5, and light from the lamp 28 passes through the blood on the slide glass 5, and via half mirrors 29 and an interference filter 210 arranged on an optical path, enters a line sensor 211 for auto-focusing in which plural pixels are arranged in a line, a sensor 212 for white blood cell (WBC) detection in which plural pixels are arranged in a line and a CCD camera 213. A white blood cell detecting section 214 composed of an FPGA, an ASIC or the like is connected to the sensor 212 for white blood cell detection and is set up to provide the output signal of the sensor 212 to the white blood cell detecting section 214. A focus calculating section 215 composed of an FPGA, an ASIC or the like is connected to the sensor 211 for auto-focusing and is set up to provide the output signal of the sensor 211 to the focus calculating section 215. White blood cell detection is performed by the white blood cell detecting section 214 on the basis of an output signal in accordance with the incident light of the sensor 212. Information to be used for the auto-focus operation is calculated by the focus calculating section 215 on the basis of an output signal in accordance with the incident light of the sensor 211. The auto-focus operation is performed on the basis of this information.

In addition, the microscope unit 2 includes a control section 216 and communication interfaces 217 and 218. The control section 216 includes a CPU and a memory, and is connected to the XY stage driving circuit 23, the objective lens driving circuit 24, the cassette transport driving circuit 26, the white blood cell detecting section 214, the focus calculating section 215 and the communication interfaces 217 and 218 so as to communicate therewith. When the control section 216 executes a control program stored in the memory, the above-described mechanisms are controlled.

The communication interface 217 is an Ethernet (registered trade name) interface. The communication interface 217 is connected to the image processing unit 3 via a communication cable so as to perform data communication therewith. In addition, the communication interface 218 is connected to the CCD camera 213 via an A/D converter 213a and is connected to the image processing unit 3 via a communication cable. An image signal (analog signal) output from the CCD camera 213 is A/D converted by the A/D converter 213a and image data (digital data) output from the A/D converter 213a is provided to the communication interface 218 to be transmitted to the image processing unit 3.

Moreover, the microscope unit 2 includes a two-dimensional bar-code reader 219. A two-dimensional bar-code indicating a specimen ID is printed on a frosted section of the slide glass 5 and the two-dimensional bar-code of the slide glass 5 introduced into the microscope unit 2 is read by the two-dimensional bar-code reader 219. In this manner, the read specimen ID is provided to the control section 216.

<Configuration of Image Processing Unit 3>

Figure 3:
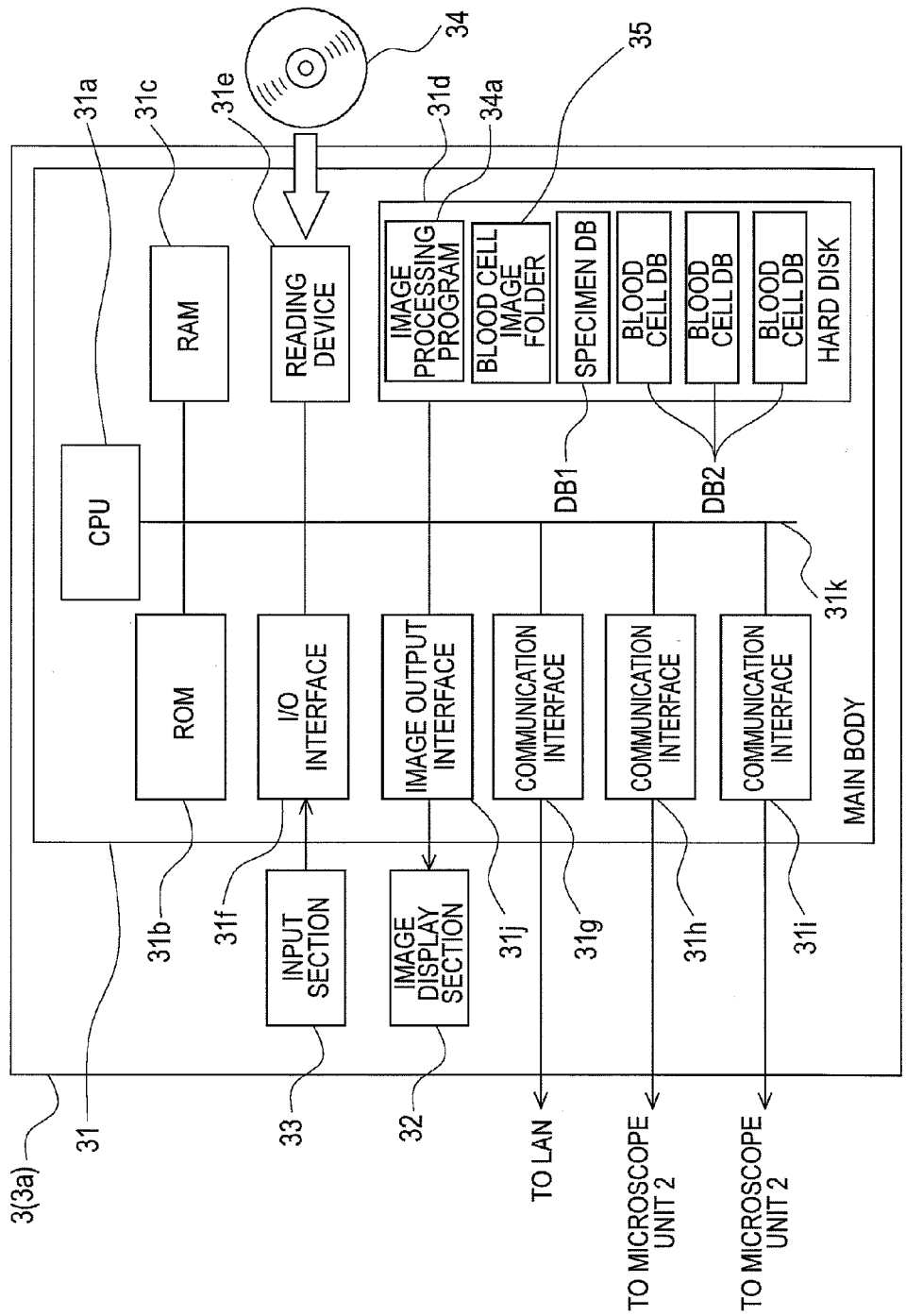
FIG. 3 is a block diagram showing the configuration of an image processing unit according to an embodiment.

Next, the configuration of the image processing unit 3 will be described. FIG. 3 is a block diagram showing the configuration of the image processing unit 3. The image processing unit 3 is realized by a computer 3a. As shown in FIG. 3, the computer 3a includes a main body 31, an image display section 32 and an input section 33. The main body 31 includes a CPU 31a, a ROM 31b, a RAM 31c, a hard disk 31d, a reading device 31e, an I/O interface 31f, a communication interface 31g and an image output interface 31j. The CPU 31a, the ROM 31b, the RAM 31c, the hard disk 31d, the reading device 31e, the I/O interface 31f, the communication interface 31g, a communication interface 31h, a communication interface 31i and the image output interface 31j are connected to one another by a bus 31k.

The CPU 31a can execute a computer program loaded to the RAM 31c. The CPU 31a executes an image processing program 34a to be described later, so that the computer 3a functions as the image processing unit 3.

The ROM 31b is composed of a mask ROM, a PROM, an EPROM, an EEPROM or the like, and the computer program which is executed by the CPU 31a and data used for the computer program are recorded therein.

The RAM 31c is composed of a SRAM, a DRAM or the like. The RAM 31c is used to read the image processing program 34a recorded in the hard disk 31d. Moreover, the RAM is used as an operating area of the CPU 31a when the CPU 31a executes a computer program.

In the hard disk 31d, various computer programs for execution by the CPU 31a, such as an operating system and an application program, and data which are used to execute the computer programs are installed. The image processing program 34a to be described later is also installed in the hard disk 31d.

The hard disk 31d is provided with a blood cell image folder 35 for storing blood cell images. In the blood cell image folder 35, a folder is provided for each specimen and blood cell images obtained as described later are stored in the folder. The folder provided for each specimen has a folder name including a specimen ID, and the corresponding folder can be specified by the specimen ID. The blood cell image folder 35 is set up so as to share data with the blood cell image display unit 4 and the blood cell image display unit 4 can access files stored in the blood cell image folder 35.

Further, the hard disk 31d is provided with a specimen database DB1 for storing information relating to specimens (hereinafter referred to as "specimen information"), and a blood cell database DB2 for storing results of the classification of white blood cells by image processing. The specimen database DB1 is a relational database and includes a field for storing specimen IDs, fields for storing the numerical data of the analysis result (the number of white blood cells, the number of red blood cells, etc.) obtained from a multiple automatic blood cell analyzing apparatus (not shown), fields for storing information on results that are determined to be abnormal by the multiple blood cell analyzing apparatus, a field for storing dates of measurements performed by the specimen imaging apparatus 1, a field for storing patients' names, a field for storing information specifying a hospital ward, a field for storing ages of the patients, a field for storing the number N of white blood cells counted by the microscope unit 2, and the like.

FIG. 4 is a schematic view showing a configuration of the blood cell database DB2. The blood cell database DB2 is provided for each specimen and each blood cell database DB2 includes data indicating a specimen ID. As a result, the blood cell database DB2 can be specified by the specimen ID. The blood cell database DB2 is provided with a white blood cell ID field F21 for storing white blood cell IDs specifying the white blood cells, a type field F22 for storing classification results of the white blood cells, and a reconfirmation object field F23 for storing information for specifying the white blood cells which cannot be classified, and fields F24, F25, . . . for storing various characteristic parameter values (the numeric values of the characteristic parameters). In the reconfirmation object field F23, "0" is stored when the white blood cells are normally classified, and "1" is stored when the white blood cells cannot be classified so as to be a reconfirmation object.

The reading device 31e is composed of a flexible disk drive, a CD-ROM drive, a DVD-ROM drive or the like and can read the computer program or data recorded in a portable recording medium 34. In the portable recording medium 34, the image processing program 34a is stored which prompts the computer to function as the image processing unit 3. The computer 3a can read the image processing program 34a from the portable recording medium 34 and install the image processing program 34a in the hard disk 31d.

The image processing program 34a is not only provided by the portable recording medium 34 but can be also provided from an external device, which is connected to the computer 3a by an electric communication line (which may be wired or wireless) to communicate therewith via the electric communication line. For example, the image processing program 34a is stored in the hard disk of a server computer on the internet and the computer 3a accesses the server computer to download the computer program and install the computer program in the hard disk 31d.

Furthermore, in the hard disk 31d, for example, a multi-tasking operating system is installed such as Windows (registered trade name) which is made and distributed by Microsoft Corporation in America. In the following description, the image processing program 34a according to this embodiment operates on the above operating system.

The I/O interface 31f is composed of, for example, a serial interface such as USB, IEEE1394 or RS-232C, a parallel interface such as SCSI, IDE or IEEE1284, and an analog interface including a D/A converter and an A/D converter. The input section 33 is composed of a keyboard and a mouse and is connected to the I/O interface 31f, and the user uses the input section 33 to input data to the computer 3a. In addition, the CCD camera 213 provided on the microscope unit 2 is connected to the I/O interface 31f, so that the images obtained by the CCD camera 213 can be captured.

The communication interfaces 31g and 31h are Ethernet (registered trade name) interfaces. The communication interface 31g is connected to the blood cell image display unit 4 via a LAN. The computer 3a can perform data communication with the blood cell image display unit 4, which is connected to the LAN by using a predetermined communication protocol, and a host computer (not shown) by the communication interface 31g. In addition, the communication interface 31h is connected to the communication interface 217 of the microscope unit 2 via a communication cable so as to perform data communication therewith.

The communication interface 31i is connected to the communication interface 218 of the microscope unit 2 via a communication cable to perform data communication therewith. Accordingly, images captured by the CCD camera 213 are received by the communication interface 31i.

The image output interface 31j is connected to the image display section 32 composed of an LCD or a CRT to output a picture signal corresponding to the image data provided from the CPU 31a to the image display section 32. The image display section 32 displays an image (screen) in accordance with an input picture signal.

<Configuration of Blood Cell Image Display Unit 4>

The blood cell image display unit 4 is configured from a computer. The blood cell image display unit 4 is connected to the image processing unit 3 via a LAN to read and display blood cell images in the blood cell image folder 35 provided in the hard disk 31d of the image processing unit 3.

Figure 5:
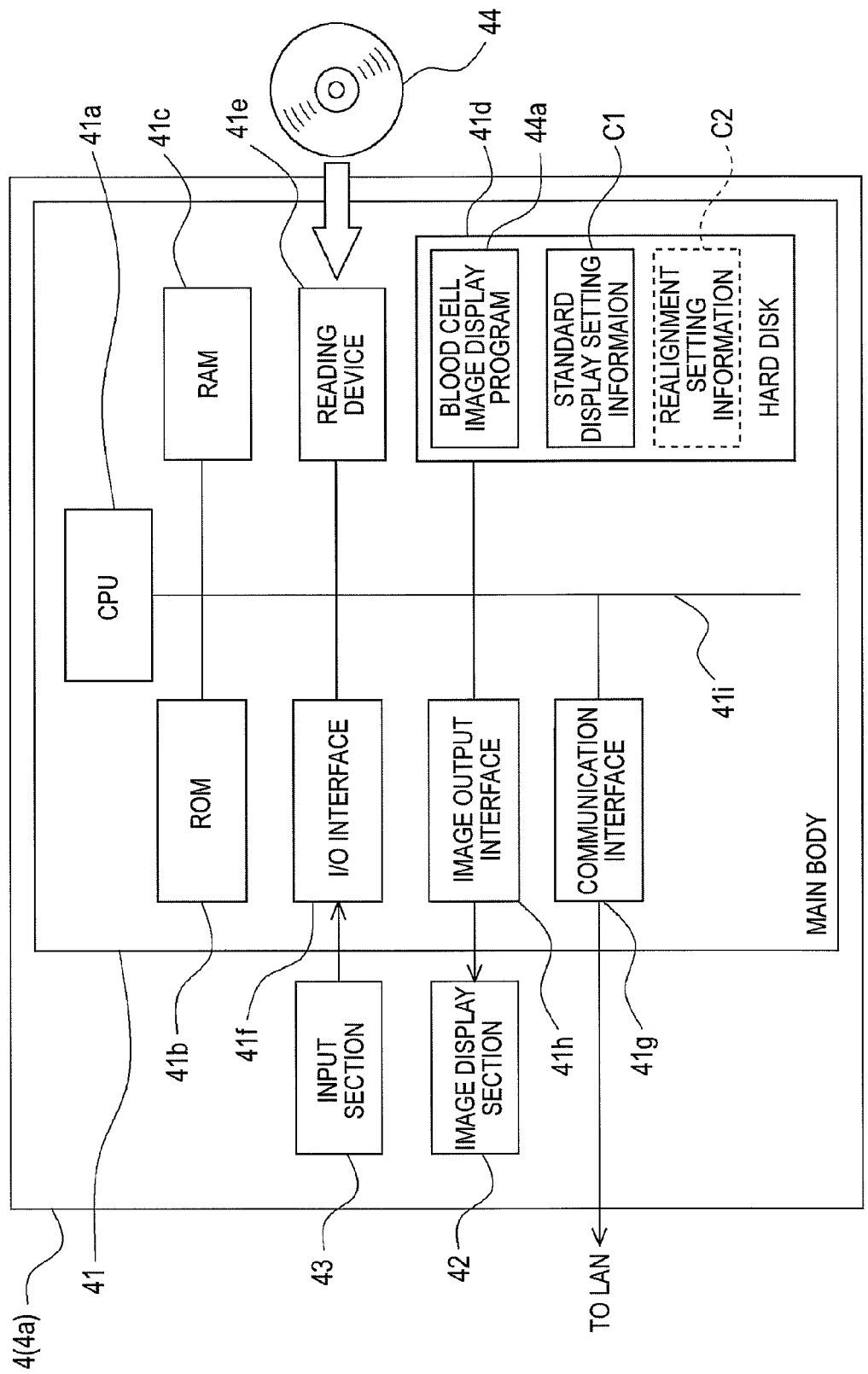
FIG. 5 is a block diagram showing the configuration of a blood cell image display unit according to an embodiment.

FIG. 5 is a block diagram showing the configuration of a blood cell image display unit 4. The blood cell image display unit 4 is realized by a computer 4a. As shown in FIG. 5, the computer 4a includes a main body 41, an image display section 42 and an input section 43. The main body 41 includes a CPU 41a, a ROM 41b, a RAM 41c, a hard disk 41d, a reading device 41e, an I/O interface 41f, a communication interface 41g and an image output interface 41h. The CPU 41a, the ROM 41b, the RAM 41c, the hard disk 41d, the reading device 41e, the I/O interface 41f, the communication interface 41g, and the image output interface 41h are connected to one another by a bus 41i.

In the hard disk 41d, various computer programs for execution by the CPU 41a, such as an operating system and an application program, and data which are used to execute the computer programs are installed. A blood cell image display program 44a to be described later is also installed in the hard disk 41d. In addition, standard display setting information C1 is stored in the hard disk 41d by a setting operation to be described later, and realignment setting information C2 is stored by a display change operation.

The reading device 41e is composed of a flexible disk drive, a CD-ROM drive, a DVD-ROM drive or the like and can read the computer program or data recorded in a portable recording medium 44. In the portable recording medium 44, the blood cell image display program 44a is stored which prompts the computer to function as the blood cell image display unit 4. The computer 4a can read the blood cell image display program 44a from the portable recording medium 44 and install the blood cell image display program 44a in the hard disk 41d.

The I/O interface 41f is composed of, for example, a serial interface such as USB, IEEE1394, SAS, SATA or RS-232C, a parallel interface such as SCSI, IDE or IEEE1284, and an analog interface including a D/A converter and an A/D converter. The input section 43 composed of a keyboard and a mouse is connected to the I/O interface 41f and the user uses the input section 43 to input data to the computer 4a.

The communication interface 41g is an Ethernet (registered trade name) interface. The communication interface 41g is connected to the image processing unit 3 via a LAN. Via the communication interface 41g, the computer 4a can send and receive data between the image processing unit 3 connected to the LAN and a host computer (not shown) by using a predetermined communication protocol.

Since the other configurations of the blood cell image display unit 4 are the same as the configurations of the above-described image processing unit 3, description thereof will be omitted.

[Operation of Specimen Imaging Apparatus]

Hereinafter, the operation of the specimen imaging apparatus 1 according to this embodiment will be described.

<Blood Cell Image Registration Operation>

First, the blood cell image registration operation will be described in which the specimen imaging apparatus 1 images the blood cells and stores the blood cell images. Before the operation of the specimen imaging apparatus 1, the preparation of the blood smears is carried out by a blood smear preparing apparatus. The blood smear preparing apparatus disposed in the vicinity of the specimen imaging apparatus 1 aspirates a specimen contained in a blood collection tube, drops the specimen on a slide glass so as to be spread, and then immerses the slide glass into a stain solution, so that the blood smear is prepared. Further, the stain which is implemented on the specimen by the blood smear preparing apparatus includes May Grunwald Giemsa stain (May Giemsa stain), Wright Giemsa stain, or Wright stain. The blood smear (slide glass 5) prepared in this way is automatically supplied to the microscope unit 2 from the blood smear preparing apparatus.

Figure 6:
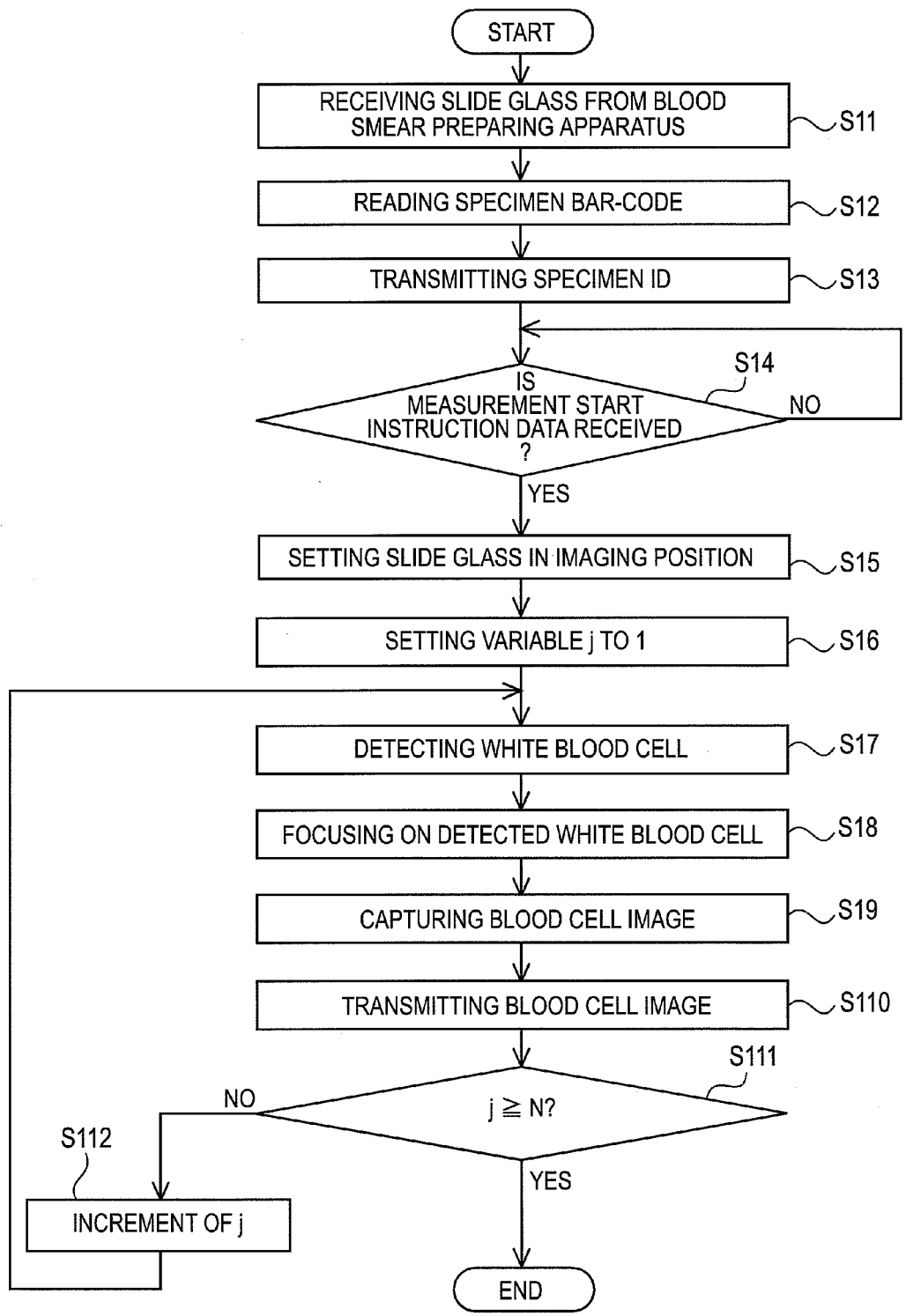
FIG. 6 is a flowchart showing the procedure of an operation of the microscope unit in a blood cell image registration operation.
Figure 7:
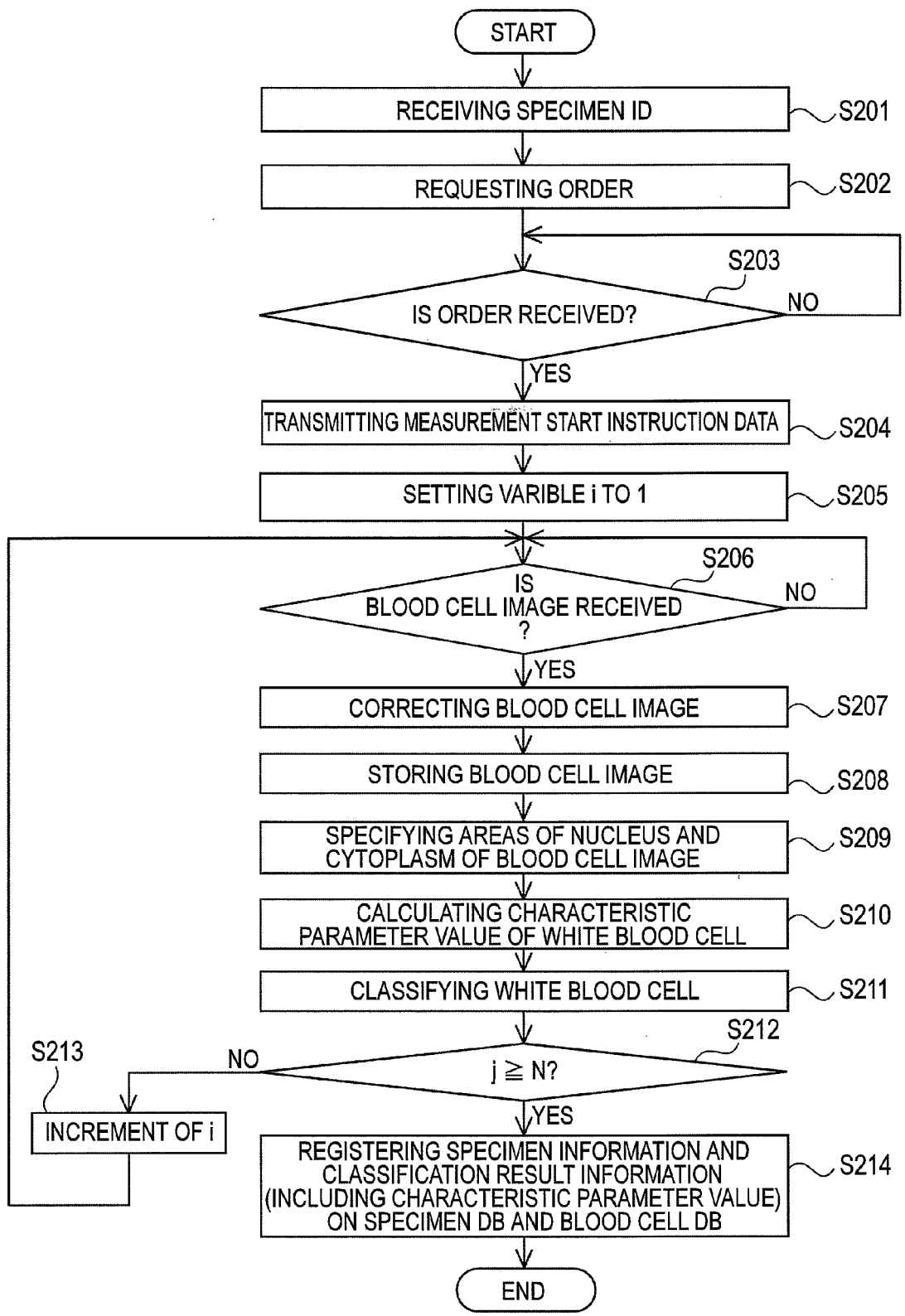
FIG. 7 is a flow chart showing the operating procedure of an image processing unit in a blood cell image registration operation.

FIG. 6 is a flowchart showing the procedure of an operation of the microscope unit 2 in the blood cell image registration operation, and FIG. 7 is a flowchart showing the process performed by the image processing unit 3 in the blood cell image registration operation. When receiving the slide glass 5 from the blood smear preparing apparatus, the microscope unit 2 detects the slide glass via a sensor (not shown) (Step S11). A control program which is executed by the control section 216 is an event-driven program. Then, in the control section 216 of the microscope unit 2, a process of Step S12 is invoked when an event occurs in which the slide glass 5 is received from the blood smear preparing apparatus.

In Step S12, the control section 216 transports the slide cassette 25 accommodating the received slide glass 5 to a predetermined bar-code reading position and the specimen bar-code is read by the two-dimensional bar-code reader 219 (Step S12). Next, the control section 216 transmits the specimen ID obtained in Step S12 to the image processing unit 3 via the communication interface 217 (Step S13).

The specimen ID transmitted from the microscope unit 2 is received by the communication interface 31h of the image processing unit 3 (Step S201 of FIG. 7). The image processing program 34a which is executed by the CPU 31a of the image processing unit 3 is an event-driven program, and in the CPU 31a, a process of Step S202 is invoked when an event occurs in which the specimen ID is received.

In Step S202, the CPU 31a transmits sequence request data including the received specimen ID to the host computer via the communication interface 31g (Step S202). The sequence transmitted from the host computer includes the specimen ID, the patient's name, the patient's sex, hospital ward information, comments, analysis results of the multiple automatic blood cell analyzing apparatus (numerical data such as the number of white blood cells and the number of red blood cells), various pieces of abnormality information detected by the multiple automatic blood cell analyzing apparatus, and the data of the number N of white blood cells counted. The CPU 31a stands by to receive the sequence (No in Step S203). When the sequence is received (Yes in Step S203), the CPU 31a transmits measurement start instruction data including the number N of white blood cells counted by the microscope unit 2 which is included in the sequence, to the microscope unit 2 (Step S204) by the communication interface 31h, and sets the variable i indicating the number of the analyzed blood cell images to 1 (Step S205).

Herein, the microscope unit 2 stands by to receive the measurement start instruction data (No in Step S14 of FIG. 6). When the measurement start instruction data transmitted from the image processing unit 3 is received by the communication interface 217 of the microscope unit 2 (Yes in Step S14), the control section 216 transports the slide cassette 25 to a predetermined position to hold the slide glass 5 which has been stopped at the predetermined position by the chuck section 27. Then, the slide glass 5 is drawn from the slide cassette 25 by retracting the chuck section 27. Then, the slide glass 5 is set at a predetermined position (imaging position) in the XY stage 21 (Step S15). In addition, the control section 216 sets a variable j indicating the number of imaging operations to 1 (Step S16).

Figure 8:
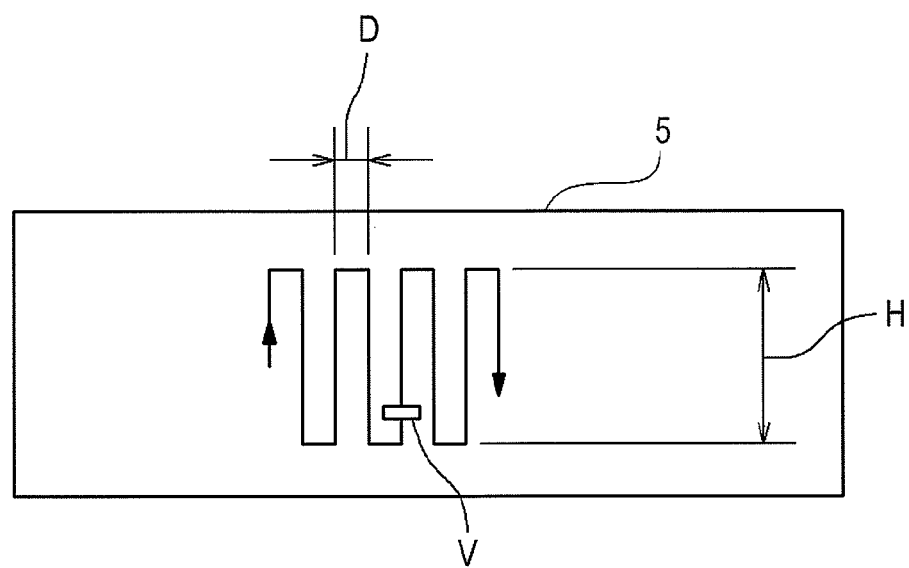
FIG. 8 is a diagram explaining a scanning pattern of a specimen on a slide glass in white blood cell detection.

Next, the white blood cells in the blood applied to the slide glass 5 are detected (Step S17) using the above-mentioned sensor 212. The sensor 212 is a line sensor and has a field of view of about 400 μm. FIG. 8 is a diagram explaining a scanning pattern of the specimen on the slide glass in the white blood cell detection. The control section 216 moves the XY stage 21 in the X and Y directions so that the sensor 212 performs a scan operation on the slide glass 5 in a substantially zigzag manner from one end toward the other end in the longitudinal direction (see FIG. 8 for reference). Generally, an interval D in the longitudinal direction of the slide glass 5 of the substantial zigzag scanning is set in the range of about 300 to 500 μm from the viewpoint of preventing detection failures and increasing scanning efficiency. A dimension H in the width direction of the slide glass 5 being scanned is set in the range of about 14 to 18 mm because the width of the slide glass 5 is normally about 26 mm.

Figure 9A:
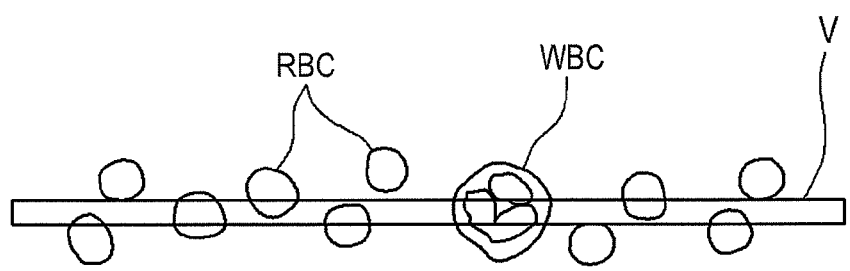
FIG. 9A is a diagram explaining the field of view of a line sensor for white blood cell detection.
Figure 9B:
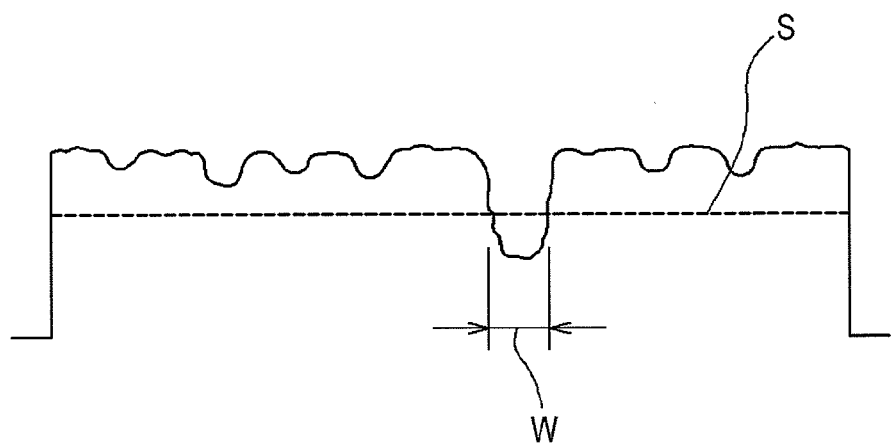
FIG. 9B is a diagram showing the signal waveform of the line sensor for white blood cell detection.

Red blood cells do not absorb much red color component of light, but the nucleus of a white blood cell does absorb a large amount of the red color component of light. Accordingly, by detecting the red color component, the white blood cells and the red blood cells can be easily distinguished by the line sensor 212. FIG. 9A is a diagram explaining the field of view of the line sensor 212, and FIG. 9B is a diagram showing a signal waveform of the line sensor 212. FIG. 9A shows that a white blood cell WBC is present in a field of view V of the line sensor 212. In this case, as shown in FIG. 9B, the red color component of a signal detected by the line sensor 212 has a value equal to or less than a reference value S in a part in which the white blood cell WBC is present. Using this phenomenon, the white blood cells can be detected in the blood. By detecting the width W of the portion in which the red color component of the signal has a value equal to or less than the reference value S, it is checked whether the portion emitting the signal is the nucleus of the white blood cell.

Next, the control section 216 performs an auto-focus operation (Step S18). As shown in FIG. 2, the direction of the light passing through the slide glass 5 and the objective lens 22 is changed by a prism mirror 29a, and the light is divided into light which is directed to the CCD camera 213 and light which is directed to the sensors 211 and 212 by the half mirrors 29. The line sensor 211 for auto-focusing is composed of two line sensors 211a and 211b.

As shown in FIG. 2, the line sensor 211a which is one of the two line sensors 211a and 211b for auto-focusing is disposed in front of (close to the objective lens on the optical path) a focus position (a position which is in focus), and the other line sensor 211b is disposed behind (far from the objective lens on the optical path) the focus position. In addition, the position of the objective lens is adjusted on the basis of a value which is obtained by the integral of the difference between the output signals of the two line sensors, so that the focus of the objective lens is on the specimen on the slide glass.

Next, the control section 216 instructs the communication interface 218 to take and transmit the image of the CCD camera 213. Thus, the image of the white blood cell detected in Step S17 is taken (Step S19) and the blood cell image is transmitted to the image processing unit 3 (Step S110). After that, the control section 216 determines whether the required counted number of the white blood cells has been satisfied, that is, whether j is equal to or greater than N (Step S111). When j is less than N (No in Step S111), the control section increments j by 1 (Step S112) and returns the process to Step S17 to repeat the detection of the white blood cells. On the other hand, when j is equal to or greater than N in Step S111 (Yes in Step S111), the control section 216 completes the process.

After the above Step S205, the CPU 31a of the image processing unit 3 stands by to receive the blood cell image (No in Step S206 of FIG. 7). When the blood cell image transmitted from the microscope unit 2 is received by the communication interface 31h of the image processing unit 3 (Yes in Step S206), the CPU 31a performs a correction process on the blood cell image (Step S207). In this correction process, the CPU 31a linearly corrects brightness values of the RGB components of all the pixels of the blood cell images such that the average value of the brightness values of the background portion (which corresponds to a portion other than the blood cells) of the blood cell images becomes a predetermined value (for example, 225). The CPU 31a stores the blood cell image after the correction in the hard disk 31d (Step S208). In the process of Step S208, a white blood cell ID corresponding to the blood cell image is generated by the CPU 31a. Then, the blood cell image is stored as image data with a file name including the white blood cell ID.

Figure 10:
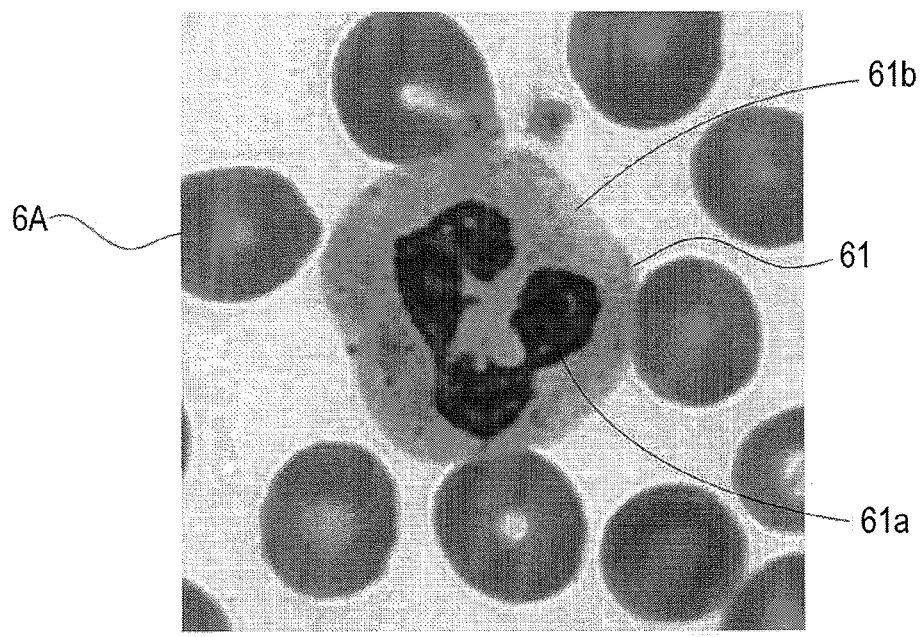
FIG. 10 is a diagram showing an example of a blood cell image.

Next, the CPU 31a specifies areas of cytoplasm and a nucleus in the blood cell image (Step S209). FIG. 10 is a diagram showing an example of the blood cell image. As shown in FIG. 10, a white blood cell image 61 is included in a blood cell image 6A. In a stained white blood cell, a nucleus has a color different from that of a cytoplasm. Moreover, the colors of the cytoplasm and the nucleus of the white blood cell are different from the colors of a red blood cell and a background. Accordingly, in the process of Step S209, a nucleus area 61a and a cytoplasm area 61b which are included in the white blood cell image 61 are specified by using a RGB value of the white blood cell image 61.

Next, the CPU 31a calculates various characteristic parameters of the white blood cell on the basis of the blood cell image (Step S210). As the characteristic parameters, there may be exemplified the area of a white blood cell nucleus, the area of the cytoplasm of a white blood cell, and the area ratio (NC ratio) between the nucleus and the cytoplasm of a white blood cell, the constriction of the nucleus, the color of the nucleus, and the color of the cytoplasm, which can be obtained on the basis of color signals (G, B, R) of the image.

Next, using the obtained characteristic parameters, the CPU 31a identifies the type of the white blood cell (Step S211). Specifically, for example, the CPU 31a sequentially compares several characteristic parameters of the white blood cell with judgment criteria values which are determined for various parameter values in advance so as to gradually narrow down the type of the white blood cell. In this manner, the imaged white blood cell is classified as a mature white blood cell such as a lymphocyte, a monocyte, an eosinophil, a basophil or a neutrophil (bacillary, lobulated), as an immature white blood cell such as a blast cell, a young granulocyte or an atypical lymphocyte, or as an erythroblast. For example, the lymphocyte has an area ratio (NC ratio) between the nucleus and the cytoplasm larger than that of the monocyte. Therefore, when a determination is made as to whether a blood cell is a lymphocyte or a monocyte, the CPU 31a determines the blood cell as a lymphocyte when the NC ratio is larger than the criteria value. The CPU 31a determines the blood cell as a monocyte when the NC ratio is less than the criteria value. In this example, the classification process is simply explained, but the classification process may be carried out using various characteristic parameters other than the NC ratio in practice.

Next, the CPU 31a determines whether the required counted number of the white blood cells has been satisfied, that is, whether i is equal to or greater than N (Step S212). When i is less than N (No in Step S212), the CPU 31a increments i by 1 (Step S213), returns the process to Step S206, and stands by to receive another blood cell image.

On the other hand, when i is equal to or greater than N in Step S212 (Yes in Step S212), the CPU 31a registers the information relating to the specimen, which is obtained as described above, in the specimen database DB1 of the hard disk 31d, and registers the classification result and the characteristic parameter values in the blood cell database DB2 (Step S214) and completes the process.

<Operation of Displaying Blood Cell Image>

Figure 11A:
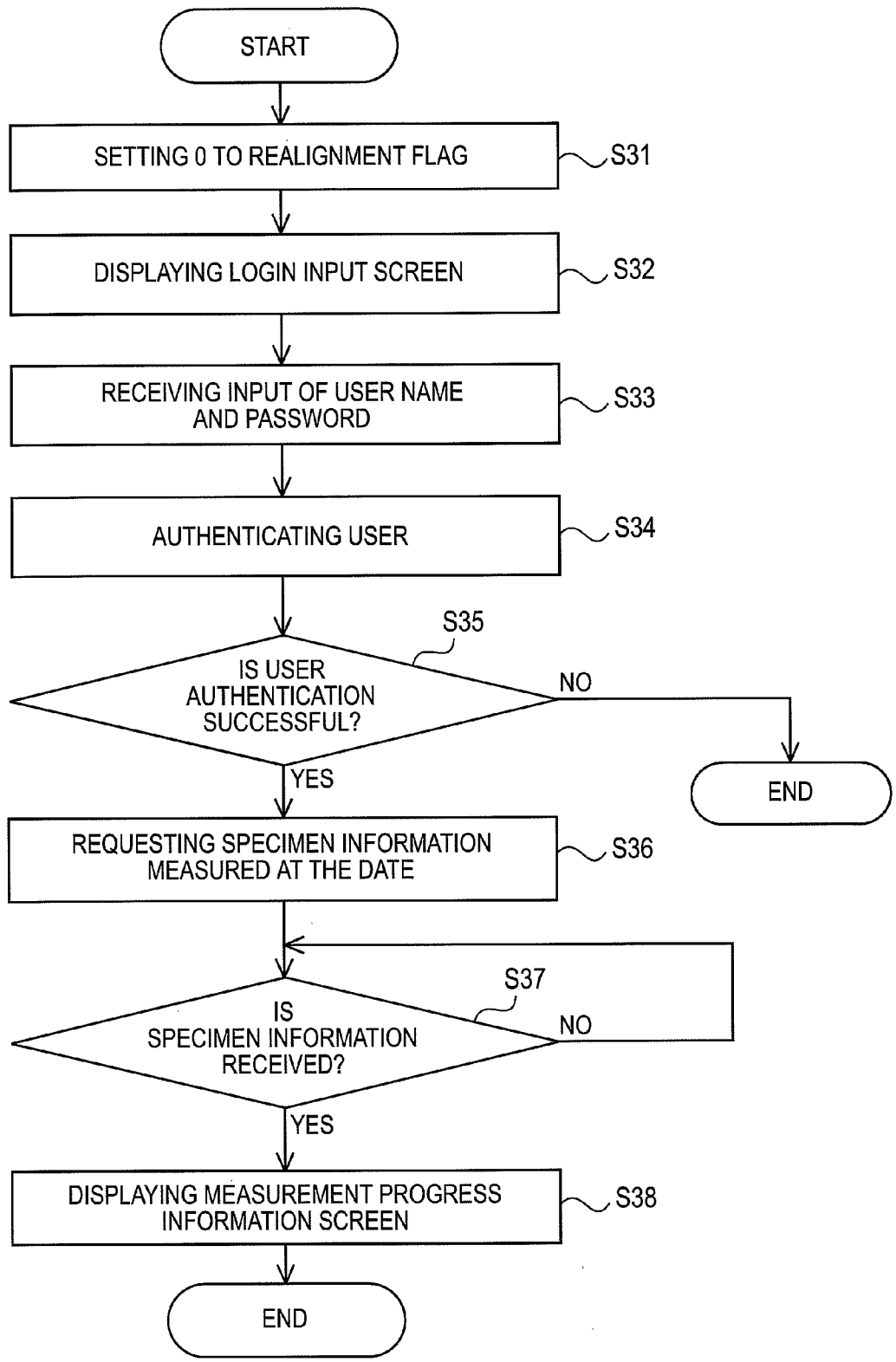
FIG. 11A is a flow chart showing the procedure of an initial operation of a blood cell image display unit in a blood cell image display operation.
Figure 11B:
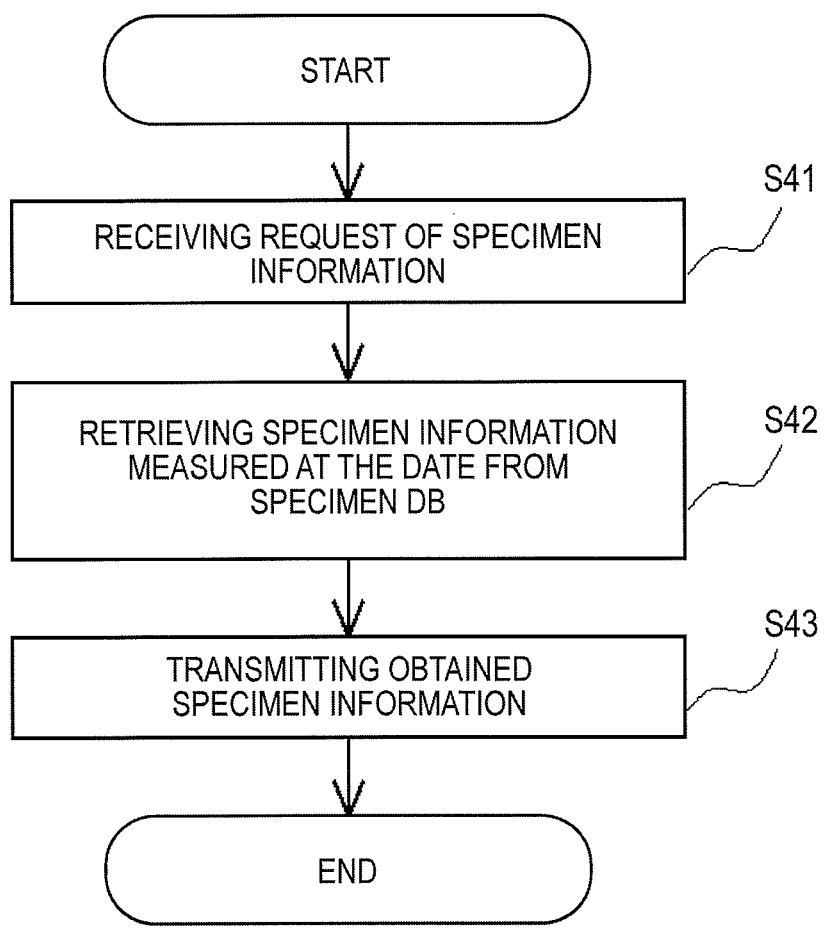
FIG. 11B is a flow chart showing the procedure of a specimen information transmitting operation of an image processing unit in a blood cell image display operation.

FIG. 11A is a flowchart showing the procedure of an initialization operation of the blood cell image display unit 4 in a blood cell image display operation, and FIG. 11B is a flowchart showing the procedure of a specimen information transmitting operation of the image processing unit 3 in the blood cell image display operation. The user operates the input section 43 of the computer 4a to instruct the execution of the blood cell image display program 44a. The CPU 41a of the computer 4a receives the instruction and executes the blood cell image display program 44a. In this manner, the computer 4a functions as the blood cell image display unit 4.

Immediately after the initiation of the blood cell image display program 44a, the CPU 41a sets an initial value of a realignment flag to "0" which is secured in the RAM 41c to be described later (Step S31 in FIG. 11A), and displays a login input screen prompting the input of a user name and a password on the image display section 42 (Step S32). In the login input screen, the CPU 41a receives a user name and a password from the user (Step S33). The blood cell image display program 44a, which is executed by the CPU 41a of the blood cell image display unit 4, is an event-driven program. Then, in the CPU 41a, a process of Step S34 is invoked when an event occurs in which the user name and the password are input.

In Step S34, the CPU 41a performs a user authentication process. When the user authentication fails (No in Step S35), the CPU 41a completes the process. When the user is successfully authenticated by using the login process (Yes in Step S35), the CPU 41a transmits request data of specimen information whose measurement date is set as the date on which the user logs in the blood image display unit 4 via the communication interface 41g to the image processing unit 3 (Step S36).

The request data transmitted from the blood cell image display unit 4 is received by the communication interface 31h of the image processing unit 3 (Step S41 of FIG. 11B). In the CPU 31a, a process of Step S42 is invoked when an event occurs in which the request data is received.

In Step S42, from the specimen database DB1, the CPU 31a obtains the specimen information whose measurement date is set as the date on which the user logs in (Step S42). Next, the CPU 31a transmits the obtained specimen information to the blood cell image display unit 4 via the communication interface 31g (Step S43) and completes the process.

Returning to FIG. 11A, after transmitting the request data of specimen information in Step S36, the CPU 41a of the blood cell image display unit 4 stands by to receive the specimen information (No in Step S37 of FIG. 11A). When the specimen information transmitted from the image processing unit 3 is received by the communication interface 41g of the blood cell image display unit 4 (Yes in Step S37), the CPU 41a displays a measurement progress screen (not shown) (Step S38), and completes the process. In the measurement progress screen, the specimen information relating to plural specimens is displayed as a list. In the measurement progress screen, the user can select one of the pieces of specimen information displayed as a list. By selecting one piece of specimen information and subsequently performing a predetermined operation (for example, the double-clicking of the left button of a mouse), the user can provide an instruction to the blood cell image display unit 4 to display a blood cell image relating to the specimen.

Figure 12A:
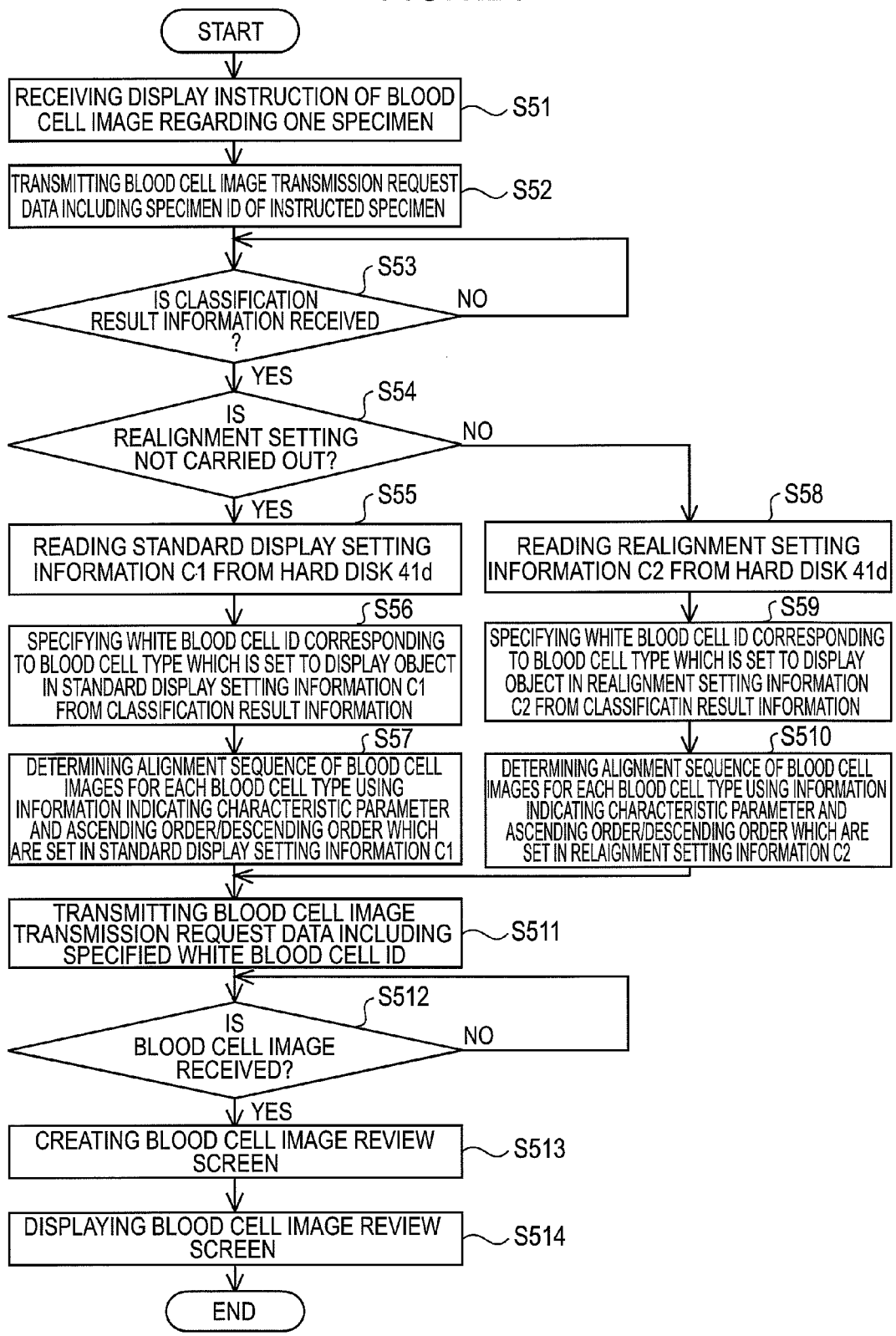
FIG. 12A is a flow chart showing the procedure of an image display operation of a blood cell image display unit in a blood cell image display operation.
Figure 12B:
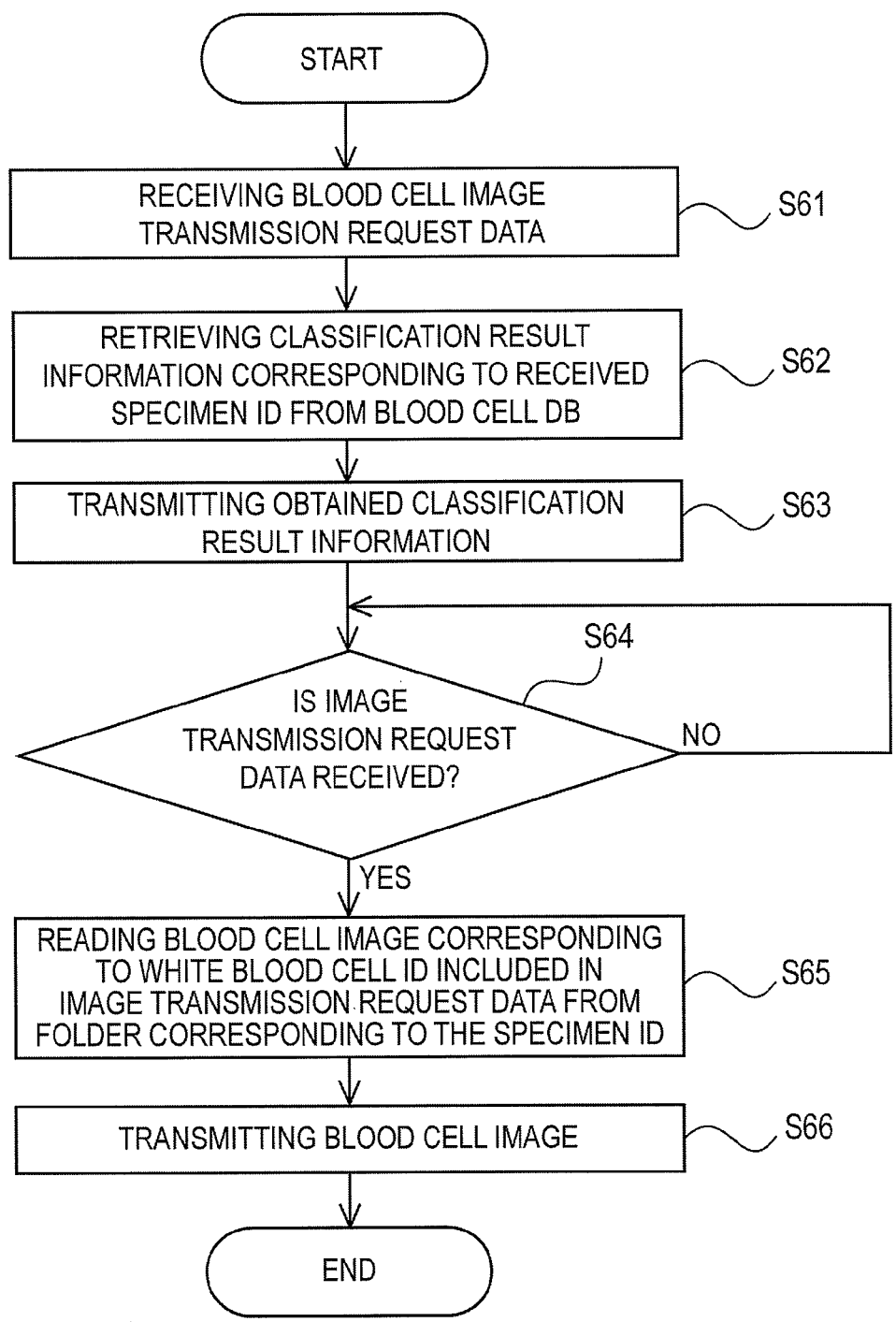
FIG. 12B is a flow chart showing the procedure of a blood cell image transmitting operation of an image processing unit in a blood cell image display operation.

FIG. 12A is a flowchart showing the procedure of an image display operation of the blood cell image display unit 4 in the blood cell image display operation, and FIG. 12B is a flowchart showing the procedure of a blood cell image transmitting operation of the image processing unit 3 in the blood cell image display operation. In the blood cell image display unit 4, when an event occurs, in which the instruction for displaying the blood cell image relating to one specimen is received as described above, in a state in which the measurement progress screen is displayed (Step S51), a process of Step S52 is invoked.

In Step S52, the CPU 41a transmits blood cell image transmitting request data, including the specimen ID of the specimen for which the instruction is made, to the image processing unit 3 via the communication interface 41g (Step S52).

The request data transmitted from the blood cell image display unit 4 is received by the communication interface 31g of the image processing unit 3 (Step S61 of FIG. 12B). In the CPU 31a, a process of Step S62 is invoked when an event occurs in which the request data is received.

In Step S62, the CPU 31a obtains classification result information from the blood cell database DB2 corresponding to the specimen ID (Step S62). The classification result information includes white blood cell IDs specifying the white blood cells shown in FIG. 4, the types (monocyte, neutrophil, basophil, eosinophil, lymphocyte, etc.) as the result of the white blood cell classification, information indicating whether or not the classification can be carried out, and various characteristic parameter values. In addition, in the classification result information, the type information or the unclassifiable information is associated with the white blood cell ID. That is, with the classification result information, the types of the white blood cells can be specified or the white blood cell can be specified as being unclassifiable or not from the white blood cell ID.

Next, the CPU 31*a* transmits the obtained classification result information to the blood cell image display unit 4 via the communication interface 31*g* (Step S63).

Returning to FIG. 12A, after transmitting the request data of the classification result information, the CPU 41*a* of the blood cell image display unit 4 stands by to receive the classification result information (No in Step S53 of FIG. 12A). When the classification result information transmitted from the image processing unit 3 is received by the communication interface 41*g* of the blood cell image display unit 4 (Yes in Step S53), the CPU 41*a* determines whether or not the realignment setting of the blood cell images is carried out as described in the following (Step S54). As to be described later, when the realignment setting of the blood cell images is carried out, the CPU 41*a* sets the realignment flag provided in the RAM 41*c* to "1". When the realignment setting of the blood cell images is not carried out, the realignment flag is set to "0". In the process of Step S54, the CPU 41*a* refers to the realignment flag so as to determine whether or not the realignment setting of the blood cell images is carried out.

In Step S54, when the realignment setting is not carried out (YES in Step S54), the CPU 41*a* reads the standard display setting information C1 from the hard disk 41*d* (Step S55). As to be described later, after the blood cell image display unit 4 is started up, when the realignment setting is not carried out, the standard display setting information C1 is used to display the blood cell images. The standard display setting information C1 includes information indicating the alignment sequence of the blood cell types, information indicating the blood cell type of the display object, information indicating the characteristic parameter which is used to determine the alignment sequence of the blood cell images for each blood cell type, and information indicating whether the alignment sequence in which the blood cell images are aligned using the characteristic parameters for each blood cell type is in ascending sequence or in descending sequence.

Next, the CPU 41*a* specifies the white blood cell IDs corresponding to the blood cell types which are set to the display objects in the standard display setting information C1 from the classification results (Step S56), and determines the alignment sequence of each white blood cell ID specified as the display object for each blood cell type using the characteristic parameters which are set in the standard display setting information C1 for each blood cell type and the information indicating that the alignment sequence is in ascending sequence or in descending sequence (Step S57). When the alignment sequence of each white blood cell ID is determined, the CPU 41*a* moves to the process in Step S511.

In Step S54, when the realignment setting is carried out (NO in Step S54), the CPU 41*a* reads the realignment setting information C2 from the hard disk 41*d* (Step S58). As to be described later, the realignment setting information C2 is used to display the blood cell images in the period from when the realignment setting of the blood cell images is carried out to until the blood cell image display unit 4 is shutdown. The realignment setting information C2 includes information indicating the alignment sequence of the blood cell types, information indicating the blood cell type of the display object, information indicating the characteristic parameters which is used to determine the alignment sequence of the blood cell images, and information indicating whether the alignment sequence in which the blood cell images are aligned using the characteristic parameters is in ascending sequence or in descending sequence.

Next, the CPU 41*a* specifies the white blood cell ID corresponding to the blood cell type which is set to the display object in the realignment setting information C2 among the blood cell types included in the received classification result information (Step S59), and determines the alignment sequence of the white blood cell ID specified as the display object using the characteristic parameters set in the realignment setting information C2 and the information indicating that the alignment sequence is in ascending sequence or in descending sequence (Step S510). When the alignment sequence of each white blood cell ID is determined, the CPU 41*a* moves to the process in Step S511.

In Step S511, the CPU 41*a* transmits image transmission request data, including the specified white blood cell ID, to the image processing unit 3 via the communication interface 41*g* (Step S511). Further, the image transmission request data includes all of the white blood cell IDs which are specified.

Returning to FIG. 12B, after transmitting the classification result information in Step S63, the CPU 31*a* of the image processing unit 3 stands by to receive the image transmitting request data (No in Step S64 of FIG. 12B). When the request data transmitted from the blood cell image display unit 4 is received by the communication interface 31*g* of the image processing unit 3 (Yes in Step S64), the CPU 31*a* reads the blood cell image corresponding to the white blood cell ID, which is included in the image transmitting request data, from the folder corresponding to the specimen ID in the blood cell image folder 35 of the hard disk 31*d* (Step S65). Then, the CPU 31*a* transmits the read blood cell image to the blood cell image display unit 4 via the communication interface 31*g* (Step S66), and completes the process.

Returning to FIG. 12A, after transmitting the image transmitting request data in Step S511, the CPU 41*a* of the blood cell image display unit 4 stands by to receive the blood cell image (No in Step S512 of FIG. 12A). When the blood cell image transmitted from the image processing unit 3 is received by the communication interface 41*g* of the blood cell image display unit 4 (Yes in Step S512), the CPU 41*a* generates a blood cell image review screen (Step S513). In the blood cell image review screen, the respective blood cell images are aligned in the sequence that is determined in Step S57 or S510. The CPU 41*a* displays the blood cell image review screen on the image display section 42 (Step S514), and completes the process.

Figure 13:
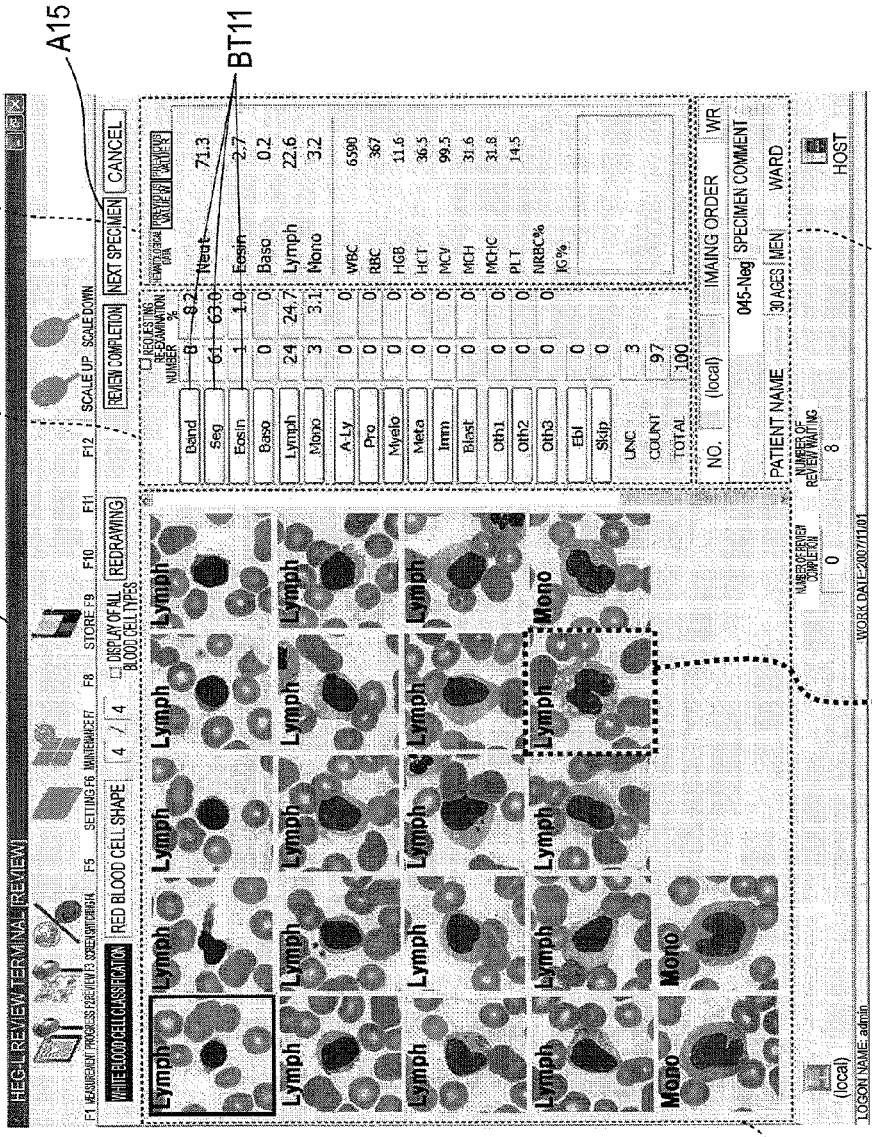
FIG. 13 is a diagram showing an example of a blood cell image review screen.

FIG. 13 is a diagram showing an example of the blood cell image review screen. In a blood cell image review screen W1, a blood cell image display area A11 for displaying one or more blood cell images, a patient information display area A12 for displaying patient information, a counted value display area A13 for displaying the result of the counting of each type of classified blood cells, and an analysis result display area A14 for displaying the analysis result of the multiple automatic blood cell analyzing apparatus are included. In the blood cell image display area, images which are obtained by reducing received blood cell images are displayed as a list. A blood cell type is displayed with a string of characters ("Mono" for a monocyte, "Band" or "Seg" for a neutrophil, "Eosin" for an eosinophil, "Baso" for a basophil, "Lymph" for a lymphocyte, etc.) in each reduced image. In addition, the blood cell images displayed in the blood cell image display area A11 are the blood cell images corresponding to the white blood cell IDs set to the display objects in Steps S56 and S59 described above. In addition, the blood cell images are displayed in each group which is created by the blood cell type.

The respective groups are aligned according to the alignment sequence of the blood cell types which are set in the standard display setting information C1 when the realignment setting is not carried out. When the realignment setting is carried out, the respective groups are aligned in a predetermined sequence. In FIG. 13, the lymphocyte and the monocyte are set as the blood cell types of the display objects, and the alignment sequence of the blood cell types is aligned such that the lymphocyte is first aligned and then the monocyte is aligned. In addition, in the blood cell image display area A11, the blood cell images are aligned in a sequence, which is set from among the ascending sequence or the descending sequence by the characteristic parameters used in determining the alignment sequence, for each blood cell type of the display object. FIG. 13 shows an example in which the blood cell images of the lymphocyte are aligned in the descending sequence with respect to the characteristic parameter "NC ratio". In addition, in the screen example shown in FIG. 13, the blood cell image of the lymphocyte disposed on the uppermost left end is the lead (the maximum NC ratio). The blood cell images of the lymphocyte are aligned in sequence of decreasing NC ratio from the lead to the right side. When reaching the right end, the sequence is lowered by one line and the blood cell images of the lymphocyte are aligned in sequence from the left end to the right side. Then, the blood cell images are aligned by repeating the sequence. Following the blood cell image of the lymphocyte with the minimum NC ratio, the blood cell images of the monocyte are aligned in the same sequence.

In the count value display area A13, plural reclassification buttons BT11 are vertically aligned on which the respective names of the blood cell types are displayed. The count values of the corresponding blood cell types are displayed in the horizontal row thereof. When one of the blood cell images displayed in the blood cell image display area A11 is selected by a click operation of the left button of a mouse, and when one of the reclassification buttons BT11 is selected in the same way, the blood cell image is reclassified as a blood cell type. The operation will be described later.

<Operation of Blood Cell Image Display Setting>

Next, as described above, the operation of the display setting of the blood cells which are stored in the image processing unit 3 will be described. In this display setting operation, the sequence of the blood cell images is set in the blood cell image review screen described above. For example, at the beginning when the specimen imaging apparatus 1 is introduced in a facility, a service man performs display setting on the blood cell image review screen, and then the setting values are used when the specimen imaging apparatus 1 is practically operated by a user. In addition, the user or the service man performs the display setting of the blood cell image screen once again, so that the setting values can be updated.

Figure 14:
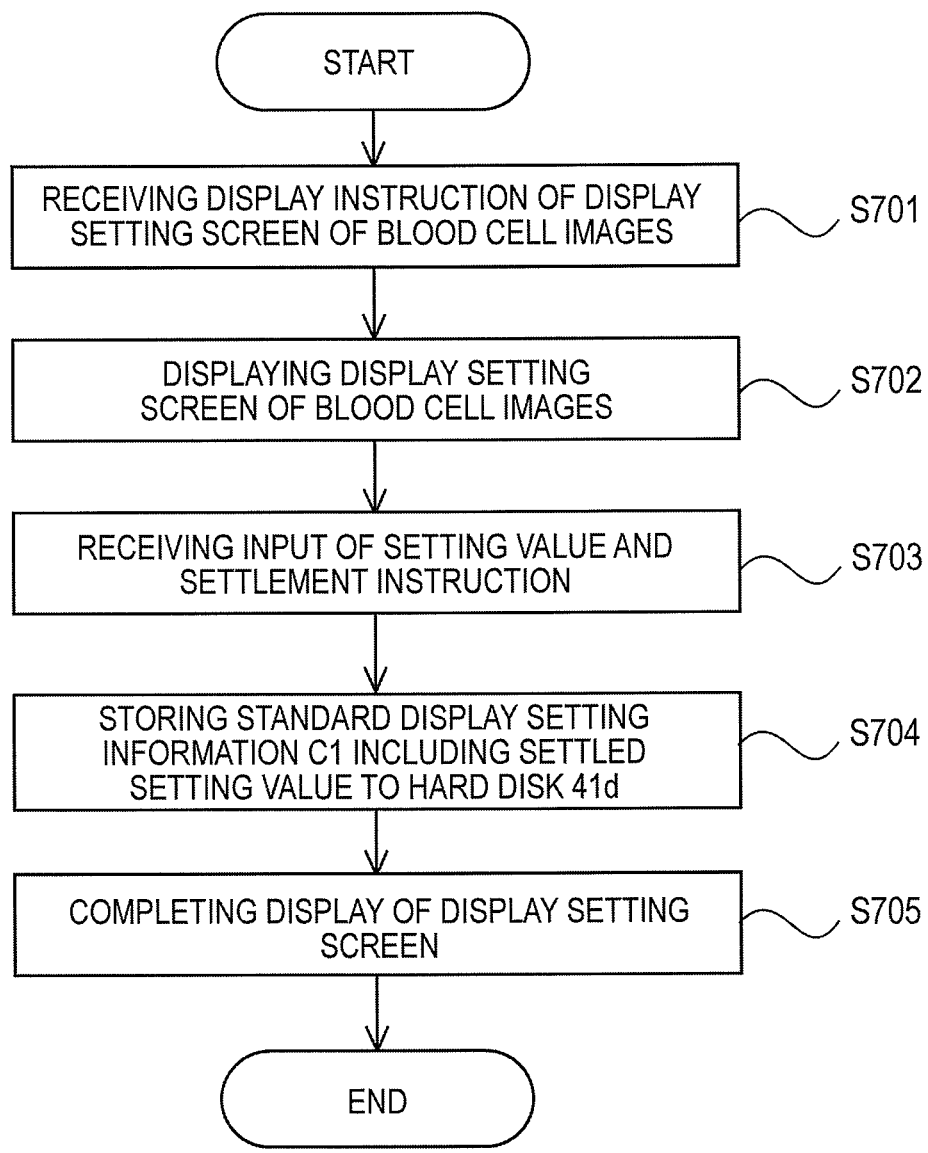
FIG. 14 is a flow chart showing a process flow of a blood cell image display unit 4 in a blood cell image display setting operation.

FIG. 14 is a flow chart showing a process flow of the blood cell image display unit 4 in the blood cell image display setting operation. An user such as the service man or the user operates the input section 43 so as to instruct the blood cell image display unit 4 to display a display setting screen W2. When the event of receiving the instruction occurs (Step S701), the CPU 41a performs the process of Step S702.

Figure 15:
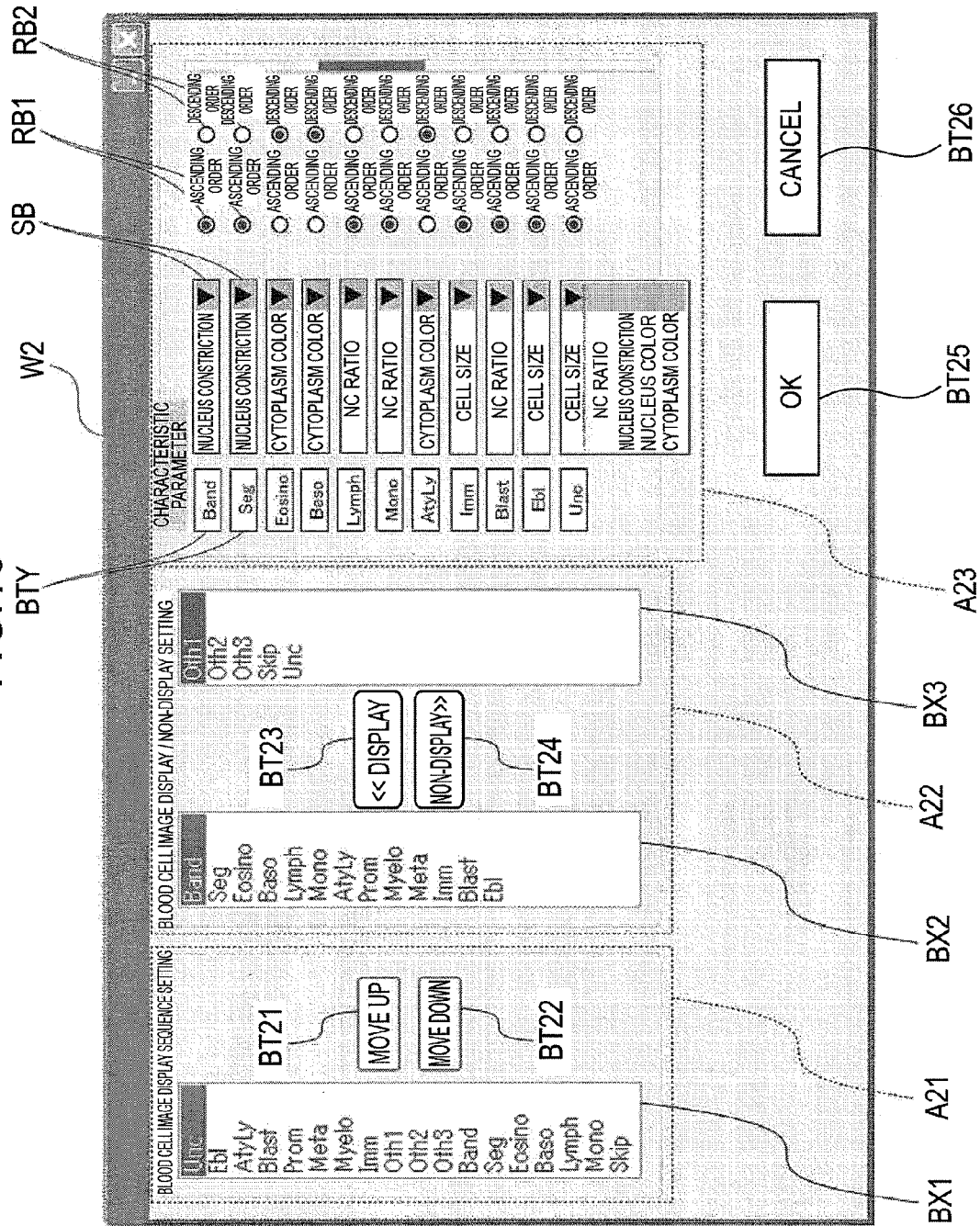
FIG. 15 is a diagram showing an example of a blood cell image display setting screen.

In Step S702, the CPU 41a displays the display setting screen W2 of the blood cell images on the image display section 42 (Step S702). FIG. 15 is a diagram showing an example of the display setting screen W2 of the blood cell images. The display setting screen W2 includes an area A21 for setting the alignment sequence of the blood cell types, an area A22 for setting the blood cell types of the display objects, and an area A23 for setting the characteristic parameters which are used to determine the alignment sequence of the blood cell images for each blood cell type.

In the area A21, a blood cell type name display box BX1 in which all the names of the blood cell types are aligned and displayed, and buttons BT21 and BT22 for changing the alignment sequence of the blood cell types are provided. In the blood cell type name display box BX1, a character string of each blood cell type name is displayed and can be selected. When the button BT21 is selected in a state where one blood cell type name is selected in the blood cell type name display box BX1 (the left button of a mouse is clicked in a state where a point of the mouse is overlapped with the button BT21), the alignment sequence of the selected blood cell type goes up by 1. On the other hand, when the button BT22 is selected in a state where one blood cell type name is selected in the blood cell type name display box BX1, the alignment sequence of the selected blood cell type goes down by 1. In this manner, the user can set the alignment sequence of the blood cell types.

In the area A22, a displaying blood cell type name display box BX2 in which the names of the blood cell types of the display objects are aligned and displayed, a non-displaying blood cell type name display box BX3 in which the names of the blood cell types of the non-display objects are aligned and displayed, and buttons BT23 and BT24 for changing display/non-display of the blood cell types are provided. In the displaying blood cell type name display box BX2, character strings of the blood cell type names of the display objects are displayed and can be selected. In the non-displaying blood cell type name display box BX3, character strings of the non-display blood cell type names of the non-display objects are displayed and can be selected. When the button BT24 is selected in a state where one blood cell type name is selected in the displaying blood cell type name display box BX2, the selected blood cell type name is deleted from the displaying blood cell type name display box BX2, and added to the non-displaying blood cell type name display box BX3. Therefore, the selected blood cell type is changed from the display object to the non-display object. On the contrary, when the button BT23 is selected in a state where one blood cell type name is selected in the non-displaying blood cell type name display box BX3, the selected blood cell type name is deleted from the non-displaying blood cell type name display box BX3, and added to the displaying blood cell type name display box BX2. Therefore, the selected blood cell type is changed from the non-display object to the display object.

In the area A23, plural blood cell type names BTY are displayed by being vertically aligned, and selection boxes SB are provided in the horizontal row thereof in sequence to select the characteristic parameters. In addition, at the horizontal row of each selection box SB, a radio button RB1 for selecting the ascending sequence as the alignment sequence and a radio button RB2 for selecting the descending sequence are provided. The blood cell type name, the selection box SB, and the radio buttons RB1 and RB2 which are aligned in one horizontal row correspond to each other. The selection button SB is provided with a pull down button. When the pull down button is selected, a selection menu is displayed in a pull down manner which includes the names of plural characteristic parameters ("Cell Size", "NC Ratio", "Nucleus Constriction", "Nucleus Color", and "Cytoplasm Color"). When the characteristic parameter desired by the user is selected by a mouse in a state where the pull down menu is displayed, the characteristic parameter is set as the characteristic parameter which is used to determine the alignment sequence of the corresponding blood cell images. In addition, the user selects any one of the radio buttons RB1 and RB2 by a mouse, so that the ascending sequence/descending sequence can be set as the alignment sequence.

In addition, in the setting screen W2, an OK button BT25 and a cancel button BT26 are provided. When the OK button BT25 is selected, the setting values which are input in the manner as described above are settled. Then, the standard display setting information C1 including the setting values is stored in the hard disk 41d. On the other hand, when the cancel button BT26 is selected, the input setting values are discarded.

The user carries out the operation as described above in a state where the display setting screen W2 of the blood cell images is displayed on the image display section 42, so that the setting values are input and the settlement can be instructed. When receiving the input and settlement of the setting values as described above (Step S703), the CPU 41a stores the standard display setting information C1 including the setting values in the hard disk 41d (Step S704), completes the displaying of the display setting screen W2 (Step S705), and completes the process. As described above, the setting is carried out on the display of the blood cell images.

<Operation of Blood Cell Image Display Change>

Next, the operation of the blood cell image display change will be described. Through the display change operation, the blood cell images can be set to be in a new alignment sequence in sequence to easily classify the blood cell images in a state where the above-mentioned blood cell review screen is displayed.

Figure 16:
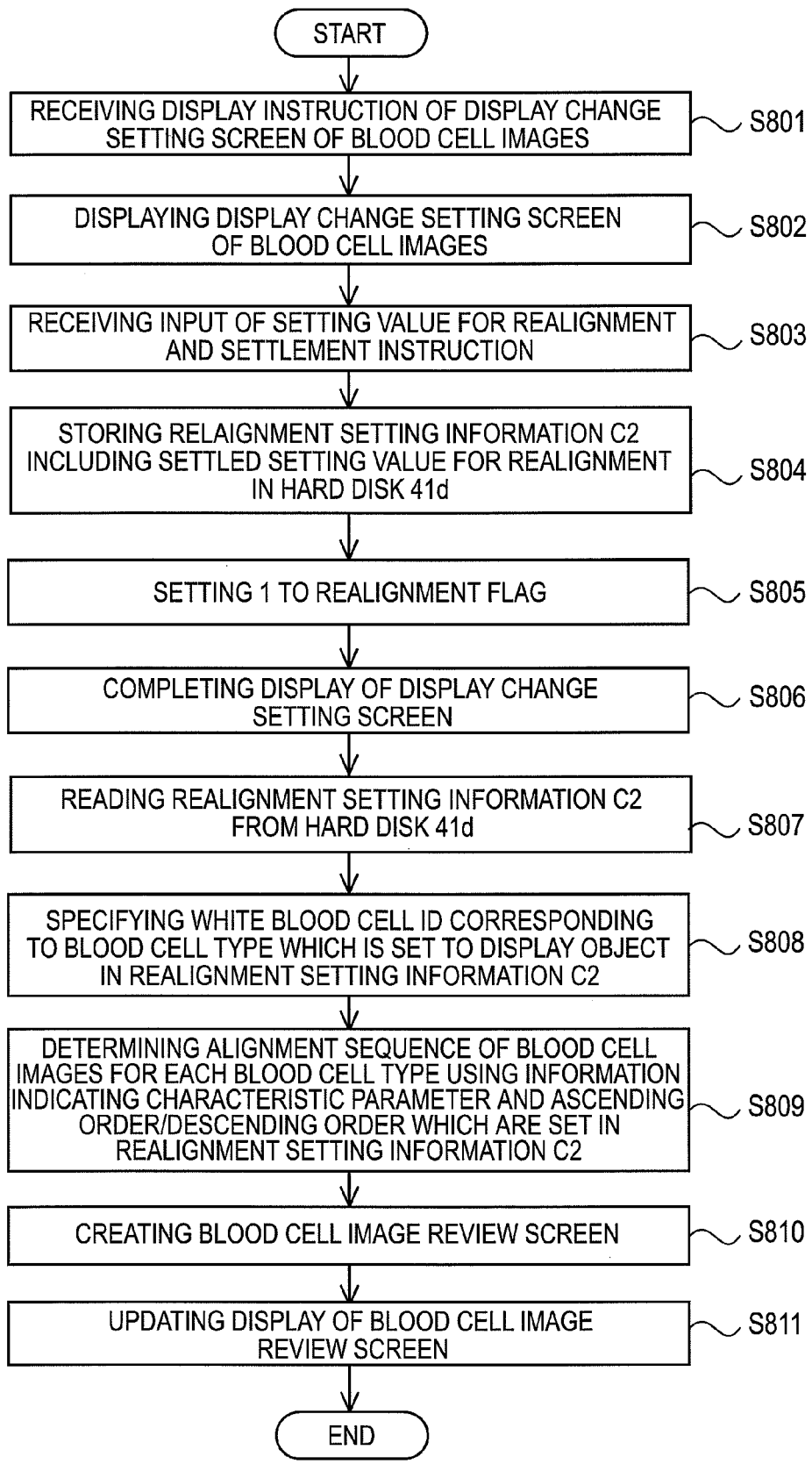
FIG. 16 is a flow chart showing a process flow of a blood cell image display unit 4 in a blood cell image display change operation.

FIG. 16 is a flow chart showing a process flow of the blood cell image display unit 4 in the blood cell image display change operation. A user operates the input section 43, for example, selects "display setting change" from the "display" menu of a menu bar, so as to instruct the blood cell image display unit 4 to display the display change setting screen of the blood cell image. When the event of receiving the instruction occurs (Step S801), the CPU 41a performs the process of Step S802.

Figure 17:
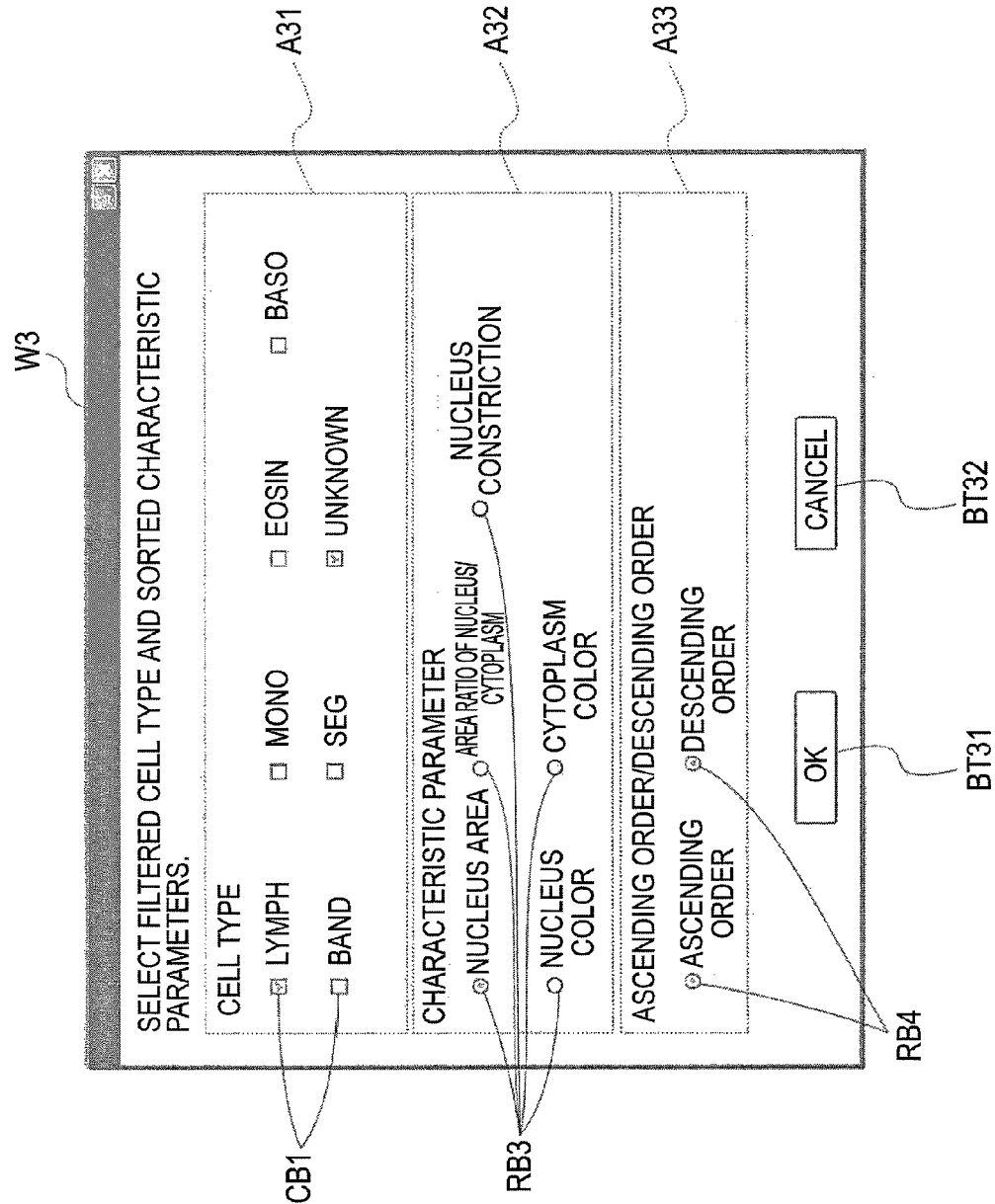
FIG. 17 is a diagram showing an example of a blood cell image display change setting screen.

In Step S802, the CPU 41a displays the display change setting screen of the blood cell images on the image display section 42 (Step S802). The display change setting screen is an independent window from the blood cell image review screen, and is overlapped with and displayed on the blood cell image review screen. FIG. 17 is a diagram showing an example of the display change setting screen of the blood cell images. The display change setting screen W3 includes an area A31 for setting the blood cell types of the display objects, an area A32 for setting the characteristic parameters which are used to determine the alignment sequence of the blood cell images, and an area A33 for setting the alignment sequence based on the characteristic parameters to be in the ascending sequence or to be in the descending sequence.

In the area A31, there are displayed the names of the respective blood cell types such as "Lympy (lymphocyte)", "Mono (monocyte)", "Eosin (eosinophil)", "Baso (basophil)", "Band (bacillary nucleus neutrophil)", "Seg (lobulated nucleus neutrophil)", and "Unknown (unclassifiable)". Further, in the horizontal row of each names described above, a check box CB1 is provided. The user selects the check box CB1 in the horizontal row of a desired blood cell type as a display object, so that the blood cell type can be set as a display object.

In the area A32, there are displayed the names of the respective characteristic parameters such as "Nucleus Area", "Nucleus/Cytoplasm Area Ratio", "Nucleus Constriction", "Nucleus Color", "Cytoplasm Color". Further, in the horizontal row of each name, a radio button RB3 is provided. A user selects the radio button RB3 in the horizontal row of a desired characteristic parameter, so that the characteristic parameter can be set which is used to determine the alignment sequence of the blood cell images.

In the area A33, there are provided radio buttons RB4 for selecting ascending sequence/descending sequence as the alignment sequence of the blood cell images. The user selects any one of two radio buttons RB4 by a mouse, so that the ascending sequence/descending sequence can be selected as the alignment sequence of the blood cell images.

In addition, in the display change setting screen W3, an OK button BT31 and a cancel button BT32 are provided. When the OK button BT31 is selected, the setting values which are input in the manner as described above are settled. Then, the realignment setting information C2 including the setting values is stored in the hard disk 41d. On the other hand, when the cancel button BT32 is selected, the input setting values are discarded.

A user carries out the operation as described above in a state where the display change setting screen of the blood cell images is displayed on the image display section 42, so that the setting values for the realignment are input and the settlement can be instructed. When receiving the input of the setting values for the realignment and settlement of the setting values as described above (Step S803), the CPU 41a stores the realignment setting information C2 including the setting values in the hard disk 41d (Step S804), sets the realignment flag to "1" (Step S805), and completes the display of the display change setting screen (Step S806). As described above, the initial value of the realignment flag is "0".

Next, the CPU 41a reads the realignment setting information C2 from the hard disk 41d (Step S807), specifies the white blood cell IDs corresponding to the blood cell types which are set to the display objects in the realignment setting information C2 from the blood cell types included in the classification result information (Step S808), and determines the alignment sequence of the white blood cell IDs specified as the display objects using the characteristic parameters, which are set in the realignment setting information C2, and the information indicating whether the alignment sequence is the ascending sequence or the descending sequence for each blood cell type (Step S809). Then, the CPU 41a creates the blood cell image review screen in which the determined blood cell images are aligned (Step S810), updates the display of the blood cell image review screen (Step S811), and completes the process. Therefore, the blood cell images are aligned in the sequence in accordance with the characteristic parameter value which is set for realignment. That is, it was difficult to differentiate which blood cell type that the blood cell image is classified into in the sequence of the blood cell images set in the display setting surface W2. However, in the realignment setting screen W3, the blood cell images are realigned in an alignment sequence which is newly set in the realignment setting screen W3, so that the accuracy in the classification of the blood cell type can be enhanced.

<Reclassification Operation of Blood Cell Image>

Figure 18A:
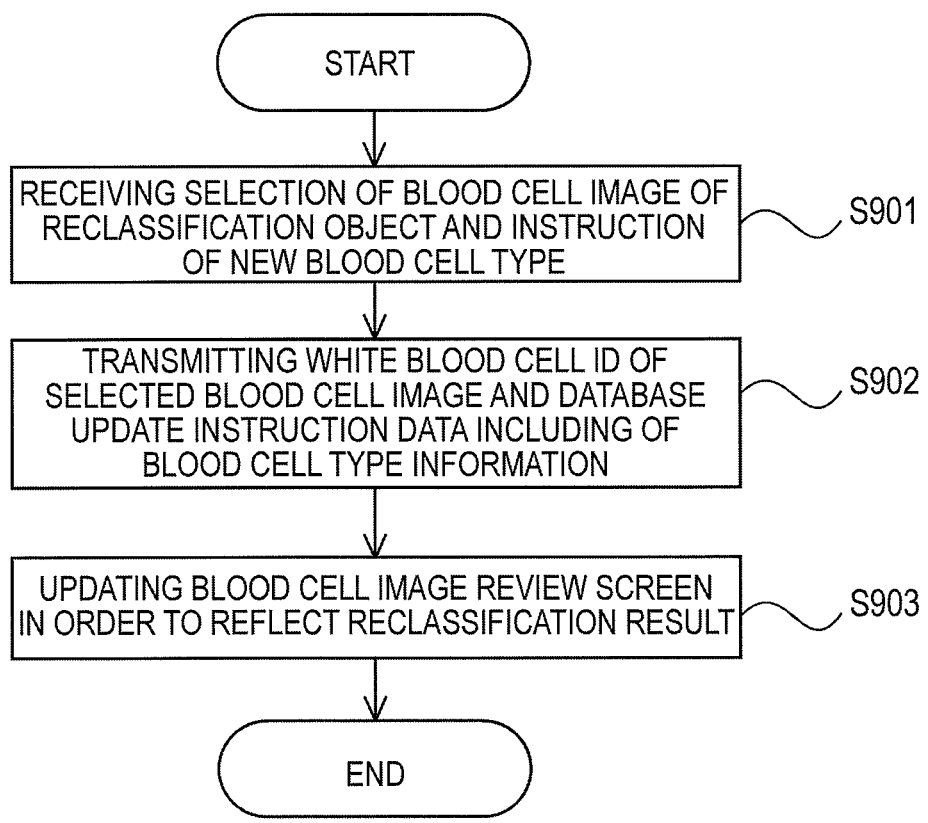
FIG. 18A is a flow chart showing a process flow of a blood cell image display unit 4 in a blood cell image reclassification operation.
Figure 18B:
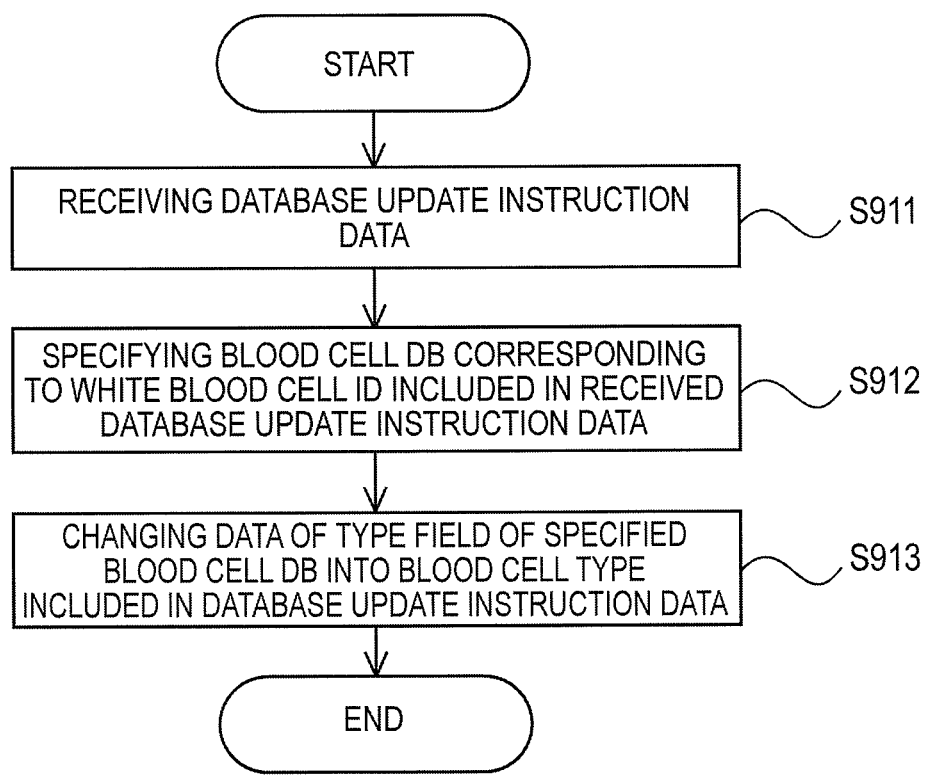
FIG. 18B is a flow chart showing a process flow of an image processing unit 3 in a blood cell image reclassification operation.

A user (a doctor or a surveyor who is a laboratory technician) refers to the blood cell image review screen, and reclassifies the erroneously classified blood cell images to be correctly classified, among the plural blood cell images aligned in the screen. Hereinafter, the operation will be described. FIG. 18A is a flow chart showing a process flow of a blood cell image display unit 4 in a blood cell image reclassification operation. FIG. 18B is a flow chart showing a process flow of an image processing unit 3 in a blood cell image reclassification operation. In a state where the blood cell image review screen is displayed, the user operates the input section 43 so as to select the blood cell image as a reclassification object, and instructs a new blood cell type of the blood cell image. The selection of the blood cell image is carried out by the clicking operation of the left button of a mouse in a state where the pointer of the mouse is overlapped with the blood cell image as the target. In addition, the instruction of the new blood cell type is carried out such that the reclassification button BT11 of the blood cell image review screen is similarly operated by the clicking operation or the like of the left button of the mouse. When an event in which the selection of the blood cell image as the reclassification object and the instruction of a new blood cell type are received occurs (Step S901), the CPU 41a performs the process of Step S902.

In Step S902, the CPU 41a transmits database update instruction data, including the white blood cell ID of the selected blood cell image and information of the new blood cell type, to the image processing unit 3 via the communication interface 41g (Step S902). In addition, the CPU 41a updates the blood cell image review screen so as to reflect the reclassification results (Step S903). In the update process of the blood cell image review screen, the reclassified blood cell image is deleted from the group of the blood cell type which is not reclassified in the blood cell image display area A11 yet (hereinafter, referred to as "old blood cell type"), and is included to the group of the blood cell type in which the blood cell image is reclassified (hereinafter, referred to as "new blood cell type"). The blood cell images belonging to the group of the new blood cell type are realigned in a sequence in accordance with the characteristic parameters which are associated with the blood cell type. In addition, the counting result of the old blood cell type is subtracted by 1, and the counting result of the new blood cell type is added by 1. Thereafter, the CPU 41a completes the process.

Figure 19:
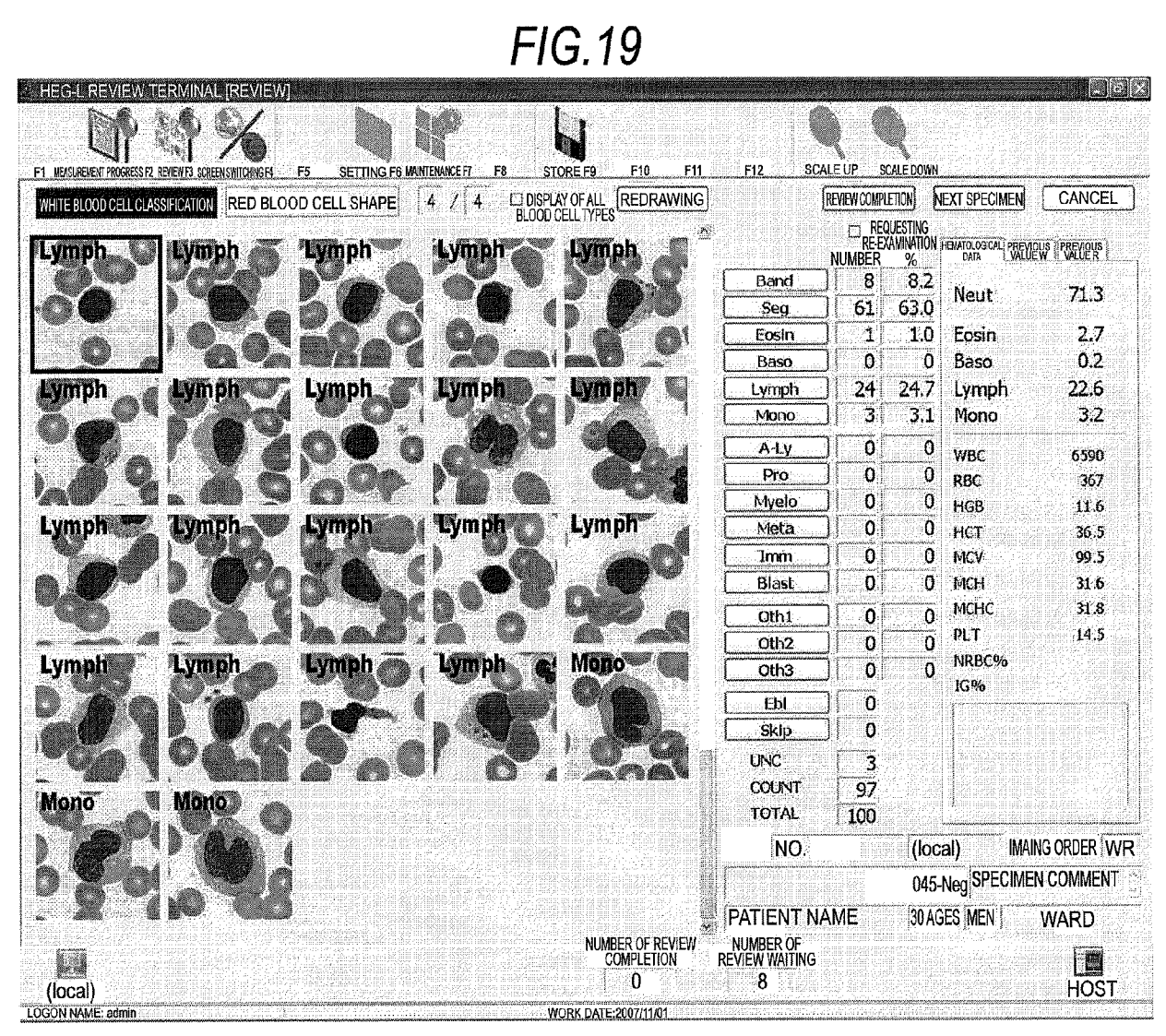

Here, while comparing the screen in which the blood cell images are aligned in imaging sequence with the screen in which the blood cell images are aligned in the sequence in accordance with the characteristic parameter values according to this embodiment, the way to reclassify the blood cell images will be described. FIG. 19 is an example of the screen in which the blood cell images are aligned in imaging sequence. Further, the screen shown in FIG. 19 has the same configuration as the blood cell image review screen shown in FIG. 13 except that the alignment sequence of the blood cell images is in imaging sequence. In addition, all the blood cell images in this screen are the same images as those displayed in the blood cell image review screen of FIG. 13. In the screen in which the blood cell images are aligned in imaging sequence as shown in FIG. 19, the adjacent blood cell images may not have a similar shape. For this reason, the surveyor such as a laboratory technician or a doctor must carefully confirm all the blood cell images and it is impossible to easily find erroneous classifications. On the other hand, in the screen in which the blood cell images are aligned in descending sequence with respect to the "NC ratio" of the characteristic parameter as shown in FIG. 13, the blood cell images with a small NC ratio among the lymphocytes with a large NC ratio are generally arranged in the latter part. In addition, as described above, since the monocyte has a NC ratio smaller than that of the lymphocyte, the blood cell images of the lymphocyte with a small NC ratio which are arranged close to the monocyte group are approximate to the shape of the monocyte, so that the blood cell images of the monocyte have a high possibility of being erroneously classified as lymphocytes. As described above, since the blood cell image of the lymphocyte which is positioned backward has a high possibility of being erroneously classified, the surveyor makes confirmations by focusing more on these images, so that the erroneous classifications can be easily found. In addition, by arranging the images as described above, the blood cell image of the blood cell type to be originally classified can be arranged in the vicinity of the blood cell image with a high possibility of being erroneously classified, so that the surveyor can easily compares the two. The surveyor compares the blood cell image with a high possibility of being erroneously classified with a blood cell image of the blood cell type to be originally classified, so that it is possible to more easily find erroneous classifications.

Figure 20A:
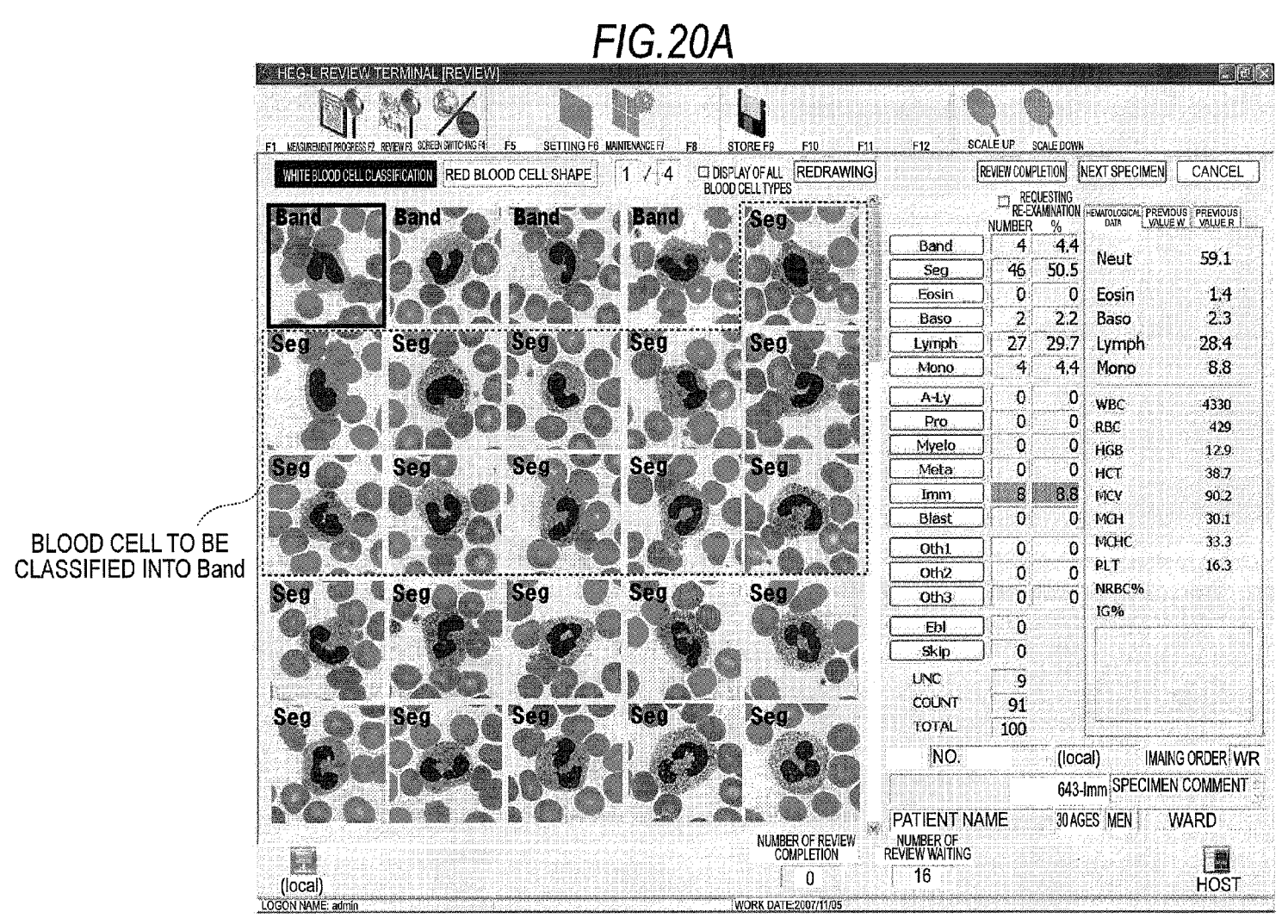
Figure 20B:
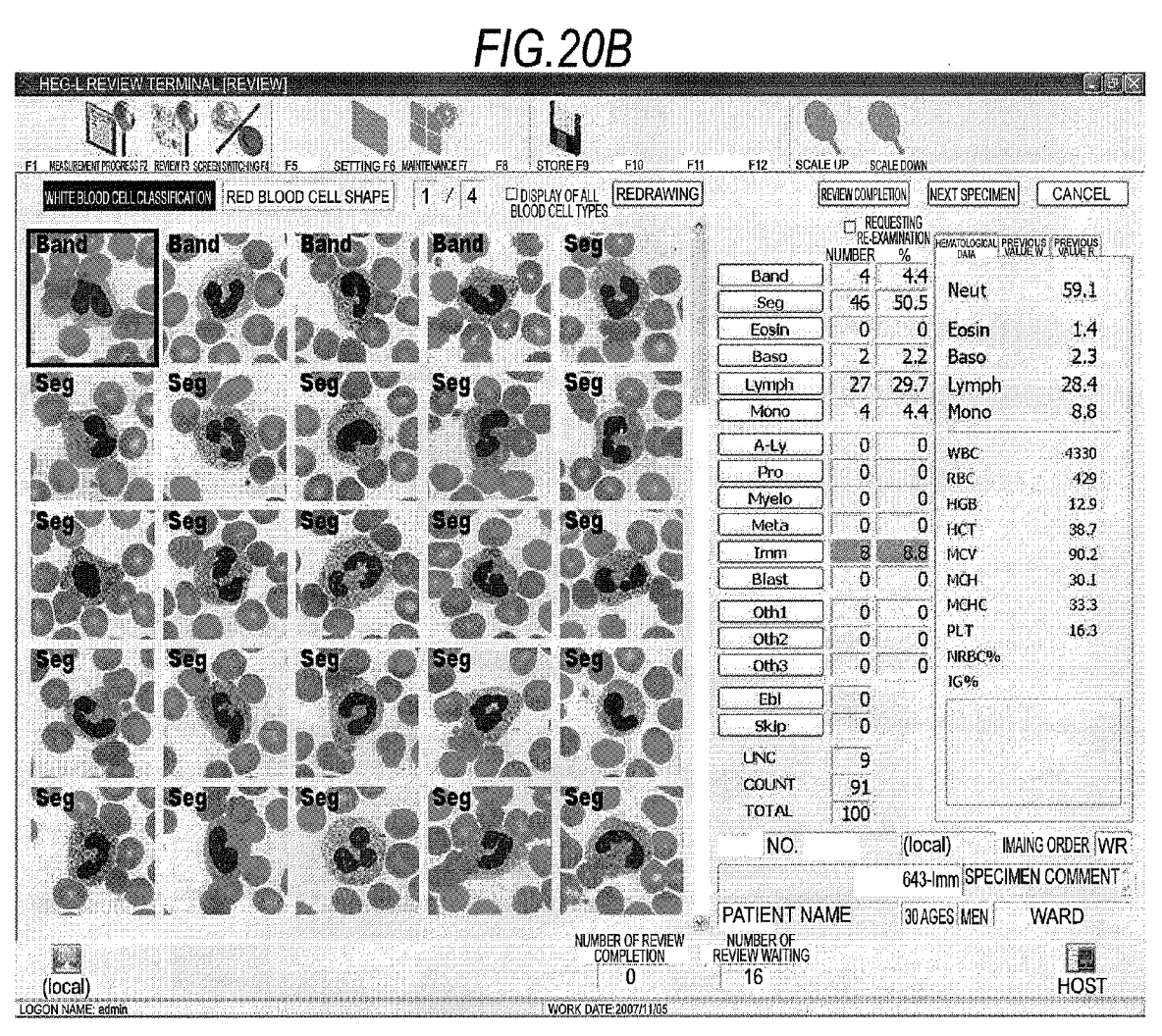

FIG. 20A is diagram showing another example of the blood cell image review screen of the specimen imaging apparatus according to the this embodiment. FIG. 20B is a diagram showing another example of the screen on which the blood cell images are aligned in imaging sequence. FIG. 20A shows an example in which the blood cell images of the respective groups of the bacillary nucleus neutrophil (Band) and the lobulated nucleus neutrophil (Seg) are aligned in descending sequence with respect to the "Nucleus Constriction" of the characteristic parameters. In the alignment sequence of the blood cell types, the bacillary nucleus neutrophil is first aligned and then the lobulated nucleus neutrophil is aligned. The "Nucleus Constriction" of the characteristic parameters indicates a minimum thickness of the nucleus. That is, the blood cell image is arranged in the fore part as the minimum thickness of the nucleus is larger and the constriction is smaller. The bacillary nucleus neutrophil has a morphological characteristic in which the nucleus is bent such that a ratio of the long diameter and the short diameter of the nucleus is equal to or more than 3:1, and the lobulated nucleus neutrophil has a morphological characteristic in which a ratio of the long diameter and the short diameter of the nucleus is lobulated to be equal to or more than that of the bacillary nucleus neutrophil. For this reason, "Nucleus Constriction" is one of the characteristic parameters which are used to classify the two. Therefore, the blood cell image with a large minimum thickness of the nucleus among the blood cell images of the lobulated nucleus neutrophil is originally the bacillary nucleus neutrophil, but it may be erroneously classified as the lobulated nucleus neutrophil. The blood cell image of the lobulated nucleus neutrophil with a large minimum thickness of the nucleus is disposed in the fore part, that is, a position close to the group of the bacillary nucleus neutrophil. In FIG. 20A, the blood cell image of the lobulated nucleus neutrophil which is surrounded with a dotted line and disposed in a position close to the group of the bacillary nucleus neutrophil, is to be classified into the bacillary nucleus neutrophil in practice. As described above, in this example, the lobulated nucleus neutrophil positioned in the fore part has a high possibility of being erroneously classified. The surveyor makes a confirmation by focusing more on these images, so that erroneous classification of the neutrophil can be easily found. On the other hand, in the screen in which the blood cell images are aligned in imaging sequence as shown in FIG. 20B, it cannot be regarded as that the blood cell images with a high possibility of being erroneously classified are assembled in one part. For this reason, the surveyor such as a laboratory technician or a doctor, must carefully confirm all the blood cell images, and it is impossible to easily find an erroneous classification.

As shown in FIG. 18B, in the CPU 31a of the image processing unit 3, when an event in which the database update instruction data is received occurs (Step S911), a process of Step S912 is invoked.

In Step S912, the CPU 31a specifies the blood cell database DB2 corresponding to the white blood cell ID which is included in the received database update instruction data (Step S912). Next, the CPU 31a changes data of the type field F22 in the specified blood cell database DB2 with a blood cell type included in the database update instruction data (Step S913), and completes the process. Therefore, the reclassification of the blood cell images is terminated.

With such a configuration as described above, in the blood cell image review screen, the blood cell images of the same blood cell type are aligned in sequence in accordance with the characteristic parameter values which are set with respect to the blood cell type. Therefore, a user can efficiently find the erroneously classified blood cell images.

In addition, when the characteristic parameter used to classify the blood cell images is used as the characteristic parameter which is used to determine the alignment sequence of the blood cell images, the blood cell images with a high possibility of being erroneously classified can be assembled in one part and a user makes confirmations by focusing more on that part. Therefore, it is possible to easily find the erroneously classified blood cell images.

In addition, when the blood cell image is classified into any one of 2 blood cell types by the magnitude of the characteristic parameter value, the groups of the blood cell images of 2 blood cell types are continuously aligned. By aligning the blood cell images in the alignment sequence matched with the alignment sequence of the 2 groups, the blood cell images with a high possibility of being erroneously classified into one blood cell type can be disposed in a position close to the other blood cell type of group into which the blood cell images should have originally been classified. To explain more specifically, when the first blood cell type of group with a large (small) characteristic parameter value is aligned in the fore part and the second blood cell type of group with a small (large) characteristic parameter value is aligned in the latter part, the blood cell images of the first blood cell type are aligned in descending (ascending) sequence with respect to the characteristic parameter, so that the blood cell images with a high possibility of being erroneously classified are disposed in a position close to the second blood cell type of group among the blood cell images of the first blood cell type of group. This is because the blood cell images with a small (large) characteristic parameter value among the blood cell images classified into the first blood cell type, that is, the blood cell images of the second blood cell type are erroneously classified into the first blood cell type in some cases. When the blood cell image suspected of erroneous classification is erroneously classified, the blood cell image can be disposed in a position close to the blood cell type of group which is considered as the group it belongs to. Therefore, a user can easily compare both groups, so that erroneous classification is more easily found.

In addition, since the characteristic parameter used to determine the alignment sequence can be freely set for each blood cell type, the characteristic parameter suitable for finding the erroneous classification can be set for each blood cell type.

In addition, the blood cell image review screen is configured to be displayed such that the standard display setting information C1 including the normally used characteristic parameter is set to the display of the blood cell image review screen in advance and the alignment sequence of the blood cell images is determined using the standard display setting information C1. Therefore, after the standard display setting information C1 is created once, even though a user does not specify the characteristic parameter which is used to determine the alignment sequence of the blood cell images, the blood cell images are displayed in the alignment sequence in which a user can easily find erroneous classification.

In addition, when a user wants to realign the alignment sequence using another characteristic parameter because the alignment sequence of the blood cell images by the standard display setting information C1 as described above is not suitable, the realignment setting of the blood cell images can be carried out. As described above, in the realignment setting, a user can set the characteristic parameter to be secondarily used, so that the blood cell images can be aligned in an alignment sequence suitable for each specimen and the erroneous classification can be more easily found. The realignment setting information C2 including the characteristic parameter to be secondarily used is not used when the blood cell image display unit 4 is shut down and then starts next time. However, after the next start, the standard display setting information C1 is reused once more. For this reason, a user does not need to carry out the display setting with the same settings as the standard display setting information C1 once more, so that the configuration is very convenient for the users.

Other Embodiments

Further, in the above-mentioned embodiments, the configuration has been described regarding the specimen imaging apparatus which images the blood smear so as to obtain the blood cell images, but the invention is not limited thereto. The specimen imaging apparatus may be configured such that tissue is gathered and sliced from a human body, attached to a slide glass, and then stained by a stain solution so as to obtain a specimen which is imaged to acquire a cell image including a cell shape.

In addition, in the above-mentioned embodiments, the configuration has been described in which even though no characteristic parameter is set which is used to determine the alignment sequence of the blood cell images immediately after the blood cell image display unit 4 starts, the alignment sequence of the blood cell images is determined in accordance with the standard display setting information C1 set once, and the blood cell image review screen is displayed. In addition, when a user carries out the realignment setting, the alignment sequence of the blood cell images is changed according to the realignment setting information C2. However, the invention is not limited to the above-mentioned configuration. It may be configured such that immediately after the blood cell image display unit 4 starts, no characteristic parameter is set which is used to determine the alignment sequence of the blood cell images, for example, the blood cell image review screen is displayed on which the blood cell images are aligned in imaging sequence. In addition, when a user carries out the realignment setting by specifying the characteristic parameter, the realignment is carried out such that the blood cell images are aligned in the alignment sequence in accordance with the characteristic parameter value.

In addition, in the above-mentioned embodiments, the configuration has been described in which after a user carries out the realignment setting and until the blood cell image display unit 4 is shut down, the arrangement sequence of the blood cell images is determined in accordance with the characteristic parameter value included in the realignment setting information C2. However, the invention is not limited to the above-mentioned configuration. It may be configured such that after a user carries out the realignment setting and until the instruction to stop the use of the realignment setting information C2 is received from the user, the arrangement sequence of the blood cell images is determined in accordance with the characteristic parameter value included in the realignment setting information C2. In addition, after the instruction to stop the use of the realignment setting information C2 is received from the user, the alignment sequence of the blood cell images is determined in accordance with the standard display setting information C1, and the blood cell image review screen is displayed. In addition, instead of until the blood cell image display unit 4 is shut down, the arrangement sequence of the blood cell images may be determined in accordance with the characteristic parameter value included in the realignment setting information C2 until a time when the state of the specimen of the display object is switched, such as a state where specimen information is switched, that is, another specimen different from the specimen which was the display object in the measurement progress screen is selected by the specimen switching button A15. In addition, the arrangement sequence of the blood cell images may be determined in accordance with the characteristic parameter value included in the realignment setting information C2 until the standard imaging apparatus 1 reaches a predetermined state other than the shutdown of the blood cell image display unit 4, such as a state where abnormality occurs in the blood cell image display unit 4 or a state where the image processing unit 3 receives a new blood cell image from the microscope unit 2.

In addition, in the above-mentioned embodiments, the configuration has been described in which the blood cell images are classified into a plurality of blood cell types and then the classification result and the blood cell images are aligned in the sequence of the characteristic parameter values. However, the invention is not limited to the above-mentioned configuration. It may be configured such that only the blood cell images of one type (lymphocyte, etc.) are imaged and the blood cell images are obtained, and the blood cell images are analyzed to obtain the characteristic parameter value (NC ratio, etc.), and the blood cell images are aligned and displayed in the sequence of the characteristic parameter values. When blood cell images of a different type (monocyte, etc.) from the type described above are included, the blood cell images are aligned in the above-mentioned sequence, so that a user can easily specify the blood cell image of a different type.

In addition, in the above-mentioned embodiments, the configuration has been described in which, by executing the blood cell image display program 44a, the computer functions as the blood cell image display unit 4 to acquire the blood cell images and the values of the characteristic parameters, to determine the alignment sequence of the blood cell images in accordance with the values of the characteristic parameters, and to display the blood cell image review screen in which the blood cell images are aligned in the alignment sequence on the image display section 42. However, the invention is not limited to this. A configuration may also be employed, in which the above-mentioned process is performed using dedicated hardware such as an FPGA, an ASIC or the like capable of executing the same process as the blood cell image display program.

In the above-described embodiments, the configuration has been described in which the above-mentioned process is carried out by the blood cell image display unit 4 which is provided independently of the image processing unit 3. However, the invention is not limited to this. A configuration may be employed in which, by one unit having the function of the image processing unit 3 as well as the function of the blood cell image display unit 4, the acquisition of the characteristic parameters by the image processing of the blood cell images, the classification of the blood cell images, the determination of the alignment sequence of the blood cell images in accordance with the values of the characteristic parameters, and the displaying of the blood cell image review screen in which the blood cell images are aligned in the alignment sequence are carried out. Further, a configuration may be employed in which, by one unit having the function of the microscope unit 2, the function of image processing unit 3, and the function of the blood cell image display unit 4, the imaging of the specimen, the acquisition of the characteristic parameters by the image processing of the blood cell images, the determination of the alignment sequence of the blood cell images in accordance with the values of the characteristic parameters, and the displaying of the blood cell image review screen in which the blood cell images are aligned in the alignment sequence are carried out.

In the above-described embodiments, the configuration has been described in which all the processes of the image processing program 34a are executed by the single computer 3a. However, the invention is not limited to this. A distribution system also can be employed for distributing the same processes as the above-described image processing program 34a to plural apparatuses (computers) and executing the processes.

In the above-described embodiments, the configuration has been described in which all the processes of the blood cell image display program 44a are executed by the single computer 4a. However, the invention is not limited to this. A distribution system also can be employed for distributing the same processes as the above-described blood cell image display program 44a to plural apparatuses (computers) and executing the processes.

What is claimed is:
1. A cell image display apparatus comprising:
a parameter value obtainer for obtaining characteristic parameter values based on a plurality of cell images obtained by imaging a sample including the plurality of cells, wherein each of the characteristic parameter values respectively indicates characteristic of each of the cells;
a type determiner for determining types of the cells based on the characteristic parameter values obtained by the parameter value obtainer;
a parameter kind receiver for receiving a designation of a kind of characteristic parameter with respect to each type of the cells, wherein the kind of the characteristic parameter is selected from the group consisting of a size of the cell, a nucleus area of the cell, a cytoplasm area of the cell, an area ratio of the nucleus area of the cell and the cytoplasm area of the cell, a nucleus color of the cell, a cytoplasm color of the cell, and a nucleus constriction of the cell;
a display;
a second parameter kind receiver for receiving designation of a kind of characteristic parameter for rearrangement in a state where the plurality of cell images are displayed on the display; and
a display controller for controlling the display so as to display the cell images in a sequence so that the cell images are arranged by the types of the cells determined by the type determiner, wherein the cell images of each type of the cells are arranged in a sequence defined by the characteristic parameter values of the kind of characteristic parameter received by the parameter kind receiver,
wherein the display controller controls the display so as to update a screen of the display to a screen where the plurality of cell images are arranged in a second sequence based on the kind of the characteristic parameter received by the second parameter kind receiver.

2. The cell image display apparatus according to claim 1, wherein the display controller controls the display so as to display, when the updated screen based on the kind of the characteristic parameter received by the second parameter kind receiver has been displayed and eliminated, a next screen where a plurality of cell images are arranged in the second sequence.

3. The cell image display apparatus according to claim 2, wherein the display controller controls the display so as to display screen where a plurality of cell images are arranged in the second sequence unless the cell image display apparatus reaches a predetermined state.

4. The cell image display apparatus according to claim 1, wherein the display controller controls the display so as to display a plurality of cell images regarding one sample, wherein the cell image display apparatus further comprises a switcher for switching a sample of a display object, and wherein the predetermined state is a state where the switcher switches the sample of the display object.

5. The cell image display apparatus according to claim 1, further comprising:
an image and type receiver for receiving selection of a cell image from the plurality of cell images displayed on the display and for receiving selection of a cell type; and
a type changer for changing a cell type of the cell image received by the image/type receiver from a cell type determined by the type determiner to the cell type received by the image and type receiver.

6. The cell image display apparatus according to claim 1, further comprising:
an imaging device for obtaining the plurality of cell images by imaging the plurality of cells.

7. The cell image display apparatus according to claim 1, wherein the parameter value obtainer obtains the plurality of characteristic parameter values from a storage device which is provided on the outside of the cell image display apparatus.

8. A cell image display apparatus comprising:
a display;
a controller being configured to perform operations, comprising:
(a) obtaining characteristic parameter values based on a plurality of cell images obtained by imaging a sample including the plurality of cells, wherein each of the characteristic parameter values respectively indicates characteristic of each of the cells;
(b) determining cell types of the cells based on the characteristic parameter values obtained in the operation (a);
(c) receiving a designation of a kind of characteristic parameter with respect to each type of the cells, wherein the kind of the characteristic parameter is selected from the group consisting of a size of the cell, a nucleus area of the cell, a cytoplasm area of the cell, an area ratio of the nucleus area of the cell and the cytoplasm area of the cell, a nucleus color of the cell, a cytoplasm color of the cell, and a nucleus constriction of the cell; and
(d) controlling the display so as to display the cell images in a sequence so that the cell images are arranged by the types of the cells determined in the operation (b), wherein the cell images of each type of the cells are arranged in a sequence defined by the characteristic parameter values of the kind of characteristic parameter received in the operation (c),
wherein the controller is configured to perform an operation (e) receiving designation of a kind of characteristic parameter for rearrangement in a state where the plurality of cell images are displayed on the display, and
wherein the operation (d) comprises an operation of updating a screen of the display to a screen where the plurality of cell images are arranged in a second sequence based on the kind of the characteristic parameter received in the operation (e).

9. The cell image display apparatus according to claim 8, wherein the controller comprises:
a first controller for performing the operations (a) and (b); and
a second controller for performing the operation (d).

10. A method of displaying a cell image comprising:
(a) obtaining characteristic parameter values based on a plurality of cell images obtained by imaging a sample including the plurality of cells, wherein each of the characteristic parameter values respectively indicates characteristic of each of the cells;
(b) determining types of the cells based on the characteristic parameter value obtained in the operation (a);
(c) receiving a designation of a kind of characteristic parameter with respect to each type of the cells, wherein the kind of the characteristic parameter is selected from the group consisting of a size of the cell, a nucleus area of the cell, a cytoplasm area of the cell, an area ratio of the nucleus area of the cell and cytoplasm area of the cell, a nucleus color of the cell, a cytoplasm color of the cell, and a nucleus constriction of the cell;
(d) a display controller for controlling the display so as to display the cell images in a sequence so that the cell images are arranged by the types of the cells determined in the operation (b), wherein the cell images of each type of the cells are arranged in a sequence defined by the characteristic parameter values of the kind of characteristic parameter received in the operation (c); and
(e) receiving designation of a kind of characteristic parameter for rearrangement in a state where the plurality of cell images are displayed on the display,
wherein the operation (d) comprises an operation of updating a screen of the display to a screen where the plurality of cell images are arranged in a second sequence based on the kind of the characteristic parameter received in the operation (e).

11. A computer program product comprising
a non-transitory computer readable medium
containing instructions stored therein adapted to enable a general purpose computer to perform operations comprising:
(a) obtaining characteristic parameter values based on a plurality of cell images obtained by imaging a sample including the plurality of cells, wherein each of the characteristic parameter values respectively indicates characteristic of each of the cells;
(b) determining types of the cells based on the characteristic parameter value obtained in the operation (a);
(c) receiving a designation of a kind of characteristic parameter with respect to each type of the cells, wherein the kind of the characteristic parameter is selected from the group consisting of a size of the cell, a nucleus area of the cell, a cytoplasm area of the cell, an area ratio of the nucleus area of the cell and the cytoplasm area of the cell, a nucleus color of the cell, a cytoplasm color of the cell, and a nucleus constriction of the cell;
(d) controlling the display so as to display the cell images in a sequence so that the cell images are arranged by the types of the cells determined in the operation (b), wherein the cell images of each type of the cells are arranged in a sequence defined by the characteristic parameter values of the kind of characteristic parameter received in the operation (c); and (e) receiving designation of a kind of characteristic parameter for rearrangement in a state where the plurality of cell images are displayed on the display, wherein the operation (d) comprises an operation of updating a screen of the display to a screen where the plurality of cell images are arranged in a second sequence based on the kind of the characteristic parameter received in the operation (e).

\* \* \* \* \*